US009340838B2

(12) United States Patent
Harmon et al.

(10) Patent No.: US 9,340,838 B2
(45) Date of Patent: May 17, 2016

(54) BRASSICA GENOMIC ASSAYS

(71) Applicant: E I DU PONT DE NEMOURS AND COMPANY, Wilmington, DE (US)

(72) Inventors: Matthew Curtis Harmon, Elkton, MD (US); Nancy L Henderson, Landenberg, PA (US); Cathy Xiaoyan Zhong, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 62 days.

(21) Appl. No.: 13/900,587

(22) Filed: May 23, 2013

(65) Prior Publication Data

US 2013/0316346 A1    Nov. 28, 2013

Related U.S. Application Data

(60) Provisional application No. 61/777,108, filed on Mar. 12, 2013, provisional application No. 61/650,623, filed on May 23, 2012.

(51) Int. Cl.
*C12Q 1/68* (2006.01)

(52) U.S. Cl.
CPC .......... *C12Q 1/6895* (2013.01); *C12Q 2600/13* (2013.01); *C12Q 2600/158* (2013.01); *C12Q 2600/166* (2013.01)

(58) Field of Classification Search
CPC .................................................... C12Q 1/6895
USPC ........................................................ 435/6.11
See application file for complete search history.

(56) References Cited

U.S. PATENT DOCUMENTS

2011/0302667 A1* 12/2011 Brown et al. .................. 800/260

FOREIGN PATENT DOCUMENTS

| CN | 101629206 | | 1/2010 | | |
|----|-----------|---|--------|---|---|
| CN | 102433379 | | 5/2012 | | |
| WO | 2011075716 | | 6/2011 | | |
| WO | WO2011075716 | * | 6/2011 | ............... | A01H 1/00 |
| WO | 2011150028 | | 12/2011 | | |
| WO | WO2011150028 | * | 12/2011 | ............... | A01H 5/00 |
| WO | 2012071039 | | 5/2012 | | |
| WO | 2012071040 | | 5/2012 | | |
| WO | WO2012071039 | * | 5/2012 | ............. | C12N 15/82 |
| WO | WO2012071040 | * | 5/2012 | ............. | C12N 15/82 |

OTHER PUBLICATIONS

Buck GA, Fox JW, Gunthorpe M, Hager KM, Naeve CW, Pon RT, Adams PS, Rush J. Design strategies and performance of custom DNA sequencing primers. Biotechniques. 1999. 27(3):528-36.*
Genbank Accession No. X87842.1, B. napus FatA gene (GI: 1143403, submitted by Loader et al. on Jun. 8, 1995, retrieved on Mar. 5, 2014 from http://www.ncbi.nlm.nih.gov/nuccore/X87842).*
Howell EC, Kearsey MJ, Jones GH, King GJ, Armstrong SJ. A and C genome distinction and chromosome identification in brassica napus by sequential fluorescence in situ hybridization and genomic in situ hybridization. Genetics. Dec. 2008;180(4):1849-57. Epub Oct. 9, 2008.*
Monsanto Biotechnology Regulatory Sciences (2004) A recommended procedure for Real-Time Quantitative TaqMan PCR for Roundup Ready Canola RT73. (http://gmo.crl.jrc.ec.europa.eu/detectionmethods/MON-Art47-perGT73rapeseed.pdf).*
Mbella et al. SYBR_Green qPCR methods for detection of endogenous reference genes in commodity crops: a step ahead in combinatory screening of genetically modified crops in food and feed products. Eur. Food Res Technol (2011) 232:485-496. Epub Jan. 2011.*
Wu G, Zhang L, Wu Y, Cao Y, Lu C. Comparison of five endogenous reference genes for specific PCR detection and quantification of Brassica napus. 2010. J Agric Food Chem 58 (5):2812-2817.*
Wu Y, Wu G, Xiao L, Lu C. Event-specific qualitative and quantitative PCR detection methods for transgenic rapeseed hybrids MS1xRF1 and MS1xRF2. J Agric Food Chem. Oct. 17, 2007; 55(21):8380-9. Epub Sep. 25, 2007.*
Suwabe K, Morgan C, Bancroft I. Integration of Brassica A genome genetic linkage map between Brassica napus and B. rapa. Genome. Mar. 2008; 51(3):169-76.*
Schelfhout CJ, Snowdon R, Cowling WA, Wroth JM. A PCR based B-genome-specific marker in *Brassica* species. Theor Appl Genet. Sep. 2004; 109(5):917-21.*
Cheung et al. Comparative analysis between homoeologous genome segments of Brassica napus and its progenitor species reveals extensive sequence-level divergence. Plant Cell. Jul. 2009; 21(7):1912-28. Epub Jul. 14, 2009.*
Akiyama H, Makiyama D, Nakamura K, Sasaki N, Minegishi Y, Mano J, Kitta K, Ozeki Y, Teshima R. A novel detection system for the genetically modified canola (*Brassica rapa*) line RT73. Anal Chem. Dec. 1, 2010; 82(23):9909-16. Epub Nov. 4, 2010.*
Genbank Accession No. X73849, B. napus (pNL2) mRNA for acyl-ACP-thioesterase (GI: 435010, submitted by Loader et al. on Jun. 30, 1993, retrieved on Mar. 20, 2014 from http://www.ncbi.nlm.nih.gov/nuccore/X73849).*
Loader NM, Woolner EM, Hellyer A, Slabas AR, Safford R. Isolation and characterization of two Brassica napus embryo acyl-ACP thioesterase cDNA clones. Plant Mol Biol. Nov. 1993; 23(4):769-78.*
Lowe T, Sharefkin J, Yang SQ, Dieffenbach CW. A computer program for selection of oligonucleotide primers for polymerase chain reactions. Nucleic Acids Res. Apr. 11, 1990; 18(7):1757-61.*
Anon., GM Crops. A Story in Numbers. Nature 2013, 497, 22-23.
James, C., A global overview of biotech (GM) crops: Adoption, impact and future prospects. GM Crops 2010, 1, 8-12.
Powles, S. B., Evolved glyphosate-resistant weeds around the world: lessons to be learnt. Pest Management Science 2008, 64, 360-365.
Castle, L. A.; Siehl, D. L.; Gorton, R.; Patten, P. A.; Chen, Y. H.; Bertain, S.; Cho, H.-J.; Duck, N.; Wong, J.; Liu, D.; Lassner, M. W., Discovery and Directed Evolution of a Glyphosate Tolerance Gene. Science 2004, 304, 1151-1154.

(Continued)

*Primary Examiner* — Samuel Woolwine
*Assistant Examiner* — Olayinka Oyeyemi

(57) ABSTRACT

Methods and compositions for detecting, identifying, and quantifying *Brassica* A genomic DNA are described. The methods are specific to the *Brassica* A genome and do not cross-react with other *Brassica* species, crops or weedy relatives that could contribute to contamination of a canola field.

16 Claims, 4 Drawing Sheets

(56) References Cited

OTHER PUBLICATIONS

Figure 1:
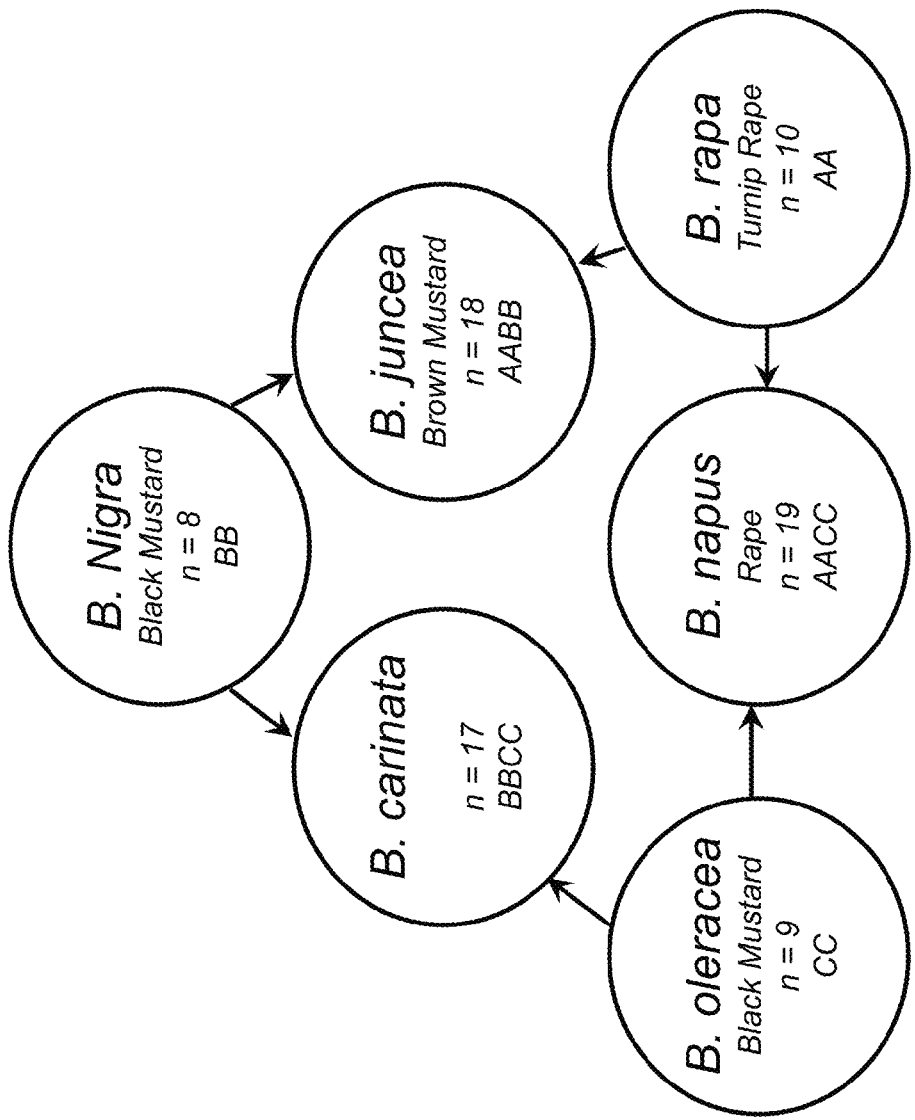

Siehl, D. L.; Castle, L. A.; Gorton, R.; Chen, Y. H.; Bertain, S.; Cho, H.-J.; Keenan, R.; Liu, D.; Lassner, M. W., Evolution of a microbial acetyltransferase for Modification of glyphosate: a novel tolerance strategy. Pest Management Science 2005, 61, 235-240.

Siehl, D. L.; Castle, L. A.; Gorton, R.; Keenan, R. J., The Molecular Basis of Glyphosate Resistance by an Optimized Microbial Acetyltransferase. Journal of Biological Chemistry 2007 282, 11446-11455.

König, A.; Cockburn, A.; Grevel, R. W. R.; Debruyne, E.; Grafstroem, R.; Hammerling, U.; Kimber, I.; Knudsen, I.; Kuiper, H. A.; Peijnenburg, A. A. C. M.; Penninks, A. H.; Poulsen, M.; Schauzu, M.; Wal, J. M., Assessment of the safety of foods derived from gentically modified (GM) crops. Food and Chemical Toxicology 2004, 42, 1047-1088.

McHughen, A.; Smyth, S., US regulatory system for genetically modified [genetically modified organism (GMO), rDNA or transgenic] crop cultivars. Plant Biotechnology Journal 2008, 6, 2-12.

Nagaharu, U., Genome-analysis in Brassica with special reference to the experimental formation of B. Napus and peculiar mode of fertilization. Japanese Journal of Botany 1935, 7, 389-452.

Weng, H.; Yang, L.; Liu, Z.; Ding, J.; Pan, A.; Zhang, D., Novel Reference Gene, High-mobility-group protein I/Y, Used in Qualitative and Real-Time Quantitative Polymerase Chain Reaction Detection of Transgenic Rapeseed Cultivars. Journal of AOAC International 2005, 88, 577-584.

Zeitler, R.; Pietsch, K.; Waiblinger, H.-U., Validation of real-time PCR methods for the quantification of transgenic contaminations in rape seed European Food Research and Technology 2002, 214, 346-351.

EU-RL-GMFF Event-specific Method for the Quantification of Oilseed Rape Line Rf3 Using Real-time PCR: Protocol. http://gmo-crl.jrc.ec.europa.eu/summaries/Rf3_validated_Method.pdf (Dec. 1).

Hernández, M.; Río, A.; Esteve, T.; Prat, S.; Pla, M., A Rapeseed-Specific Gene, Acetyl-CoA Carboxylase, Can Be Used as a Reference for Qualitative and Real-Time Quantitative PCR Detection of Transgenes from Mixed Food Samples. Journal of Agricultural and Food Chemistry 2001, 49, 3622-3627.

Doyle, J. J.; Doyle, J. L., A rapid isolation procedure for small quantities of fresh leaf tissue. Phytochemical Bulletin 1987, 19, 11-15.

James, D.; Schmidt, A-M.; Wall, E.; Green, M.; Masri, S., Reliable Detection and Identifidaiton of Genetically Modified Maize, Soybean, and Canola by Multiplex PCR Analysis. Journal of Agricultural and Food Chemistry 2003, 51, 5829-5834.

Howell EC, Kearsey MJ, Jones GH, King GJ, Armstrong SJ. A and C genome distinction and chromosome identification in brassica napus by dequential fluorescence in situ hybridization and genomic in situ hybridization. Genetics. Dec. 2008;180(4):1849-57, Epub Oct. 9, 2008.

Monsanto Biotechnology Regulatory Sciences (2004) A recommended procedure for Real-Time Quantititive TaqMan PCR for Roundup Ready Canola RT73. (http://gmo.crl.jrc.ec.europa.eu/detectionmethods/MON-Art47-pcrGT73rapeseseed.pdf).

Mbella et al. SYBR_Green qPCR methods for detection of endogenous reference genes in commodity crops: a step ahead in combinatory screening of genetically modified crops in food and feed products. Eur. Food Res Techno I (2011) 232:485-496. Epub Jan. 2011.

Wu Y, Wu G, Xiao L, Lu C. Event-specific qualitative and quantitative PCR detection methods for transgenic rapeseed bybrids MS1 xRF1 and MS1 xRF2. J Agric Food Chem. Oct. 17, 2007; 5(21 ):8080-9. Epub Sep. 25, 2007.

Suwabe K, Morgan C, Bancroft I. Integration of Brassica A genome genetic linkage map between Brassica napus and B. rapa. Genome. Mar. 2008; 51 (3):169-76.

Schelfhout CJ, Snowdon R, Cowling WA, Wroth JM. A PCR based B-genome-specific marker in *Brassica* species. Theor Appl Genet. Sep. 2004; 1 09(5):917-21.

Cheung et al. Comparative analysis between homoeologous genome segments of Brassica napus and its progenitor species reveals extensive sequence-level divergence. Plant Cell. Jul. 2009; 21 (7):1912-28 Epub Jul. 14, 2009.

Akiyama H, Makiyama D, Nakamura K, Sasaki N, Minegishi Y, Mano J, Kitta K, Ozeki Y, Teshima R. A novel detection system for the gentically modified canola (*Brassica rapa*) line RT73. Anal Chem. Dec. 1, 2010; 82(23):9909-16. Epub Nov. 4, 2010.

Genbank Accession No. X73849, B. napus (pNL2) mRNA for acyi-ACP-thioesterase (GI: 435010, submitted by Loader et al. on Jun. 30, 1993, retrieved on Mar. 20, 2014 from http://www.ncbi.nlm.nih.gov/nuccore/X73849), Loader NM, Woolner EM, Hellyer A, Slabas AR, Safford R. Isolation and characterization of two Brassica napus embryo acyl-ACP thioesterase eDNA clones. Plant Mol Bioi. Nov. 23, 1993(4):769-78.

PCT/US2013/042470 filed May 23, 2013.

Cheng, Feng et al., Biased gene fractionation and dominant gene expression among the subjenomes of Brassica rapa, PLOS ONE, vol. 7:5, E36442, May 2, 2012, pp. 1-9.

Genbank Accession No. EV080417, Brassica napus cDNA, XP002699929, Jul. 6, 2007.

Genbank Accession No. HN196531, Arabidopsis lyrata genomic sequence, XP002699930, Aug. 27, 2010.

PCT/US2013/042470 Search Report.

\* cited by examiner

FIG. 2 B

| | B. napus AACC n=18 | B. rapa AA n=11 | B. juncea AABB n=10 | B. oleracea CC n=10 | B. nigra BB n=2 | B. carinata BBCC n=2 |
|---|---|---|---|---|---|---|
| A1 | 15 | - | 10 | - | - | - |
| A2 | 2 | 2 | - | - | - | - |
| A3 | - | 3 | - | - | - | - |
| A1 and A2 | 1 | 1 | - | - | - | - |
| A1 and A3 | - | 3 | - | - | - | - |
| A2 and A3 | - | 1 | - | - | - | - |
| A1, A2 and A3 | - | 1 | - | - | - | - |
| B | - | - | 10 | - | 2 | 2 |
| C1 | 18 | - | - | 4 | - | - |
| C2 | - | - | - | 3 | - | 2 |
| C1 and C2 | - | - | - | 3 | - | - |

FIG. 3

SEQUENCE LISTING

<160> NUMBER OF SEQ ID NOS: 54

<210> SEQ ID NO 1
<211> LENGTH: 453
<212> TYPE: DNA
<213> ORGANISM: Brassica napus

<400> SEQUENCE: 1

```
aagttcggga cgagtacttg gttttctgtc ctcgagaacc caggtgaaga agaatcatca      60
tgcttccctt ataattgcta gttaaacagt taatatttaa gcatgtggat ctcaacctgt     120
tgttctctgt atttctcgta gactagcgtt tccagaagag aacaatagca gcttaaagaa     180
aatcccaaaa ctagaagatc cagctcagta ttctatgcta gagcttaagc ctcggcgagc     240
tgatctggac atgaaccagc acgtgaataa cgtcacctac attggatggg tgcttgaggt     300
gagtacctta ataaagccta caaaacgtct atcattttaa tcatacatat gagctaacta     360
actattaaat ttgagtttgg ttccctggta atggcagagc atacctcaag aaatcattga     420
tacgcatgag cttcaagtta taactctaga tta                                   453
```

<210> SEQ ID NO 2
<211> LENGTH: 453
<212> TYPE: DNA
<213> ORGANISM: Brassica rapa

<400> SEQUENCE: 2

```
aagttcggga cgagtacttg gttttctgtc ctcgagaacc caggtgaaga agaatcatca      60
tgcttccctt ataattgcta gttaaacagt taatatttaa gcatgtggat ctcaacctgt     120
tgttctctgt atttctcgta gactagcgtt tccagaagag aacaatagca gcttaaagaa     180
aatcccaaaa ctagaagatc cagctcagta ttctatgcta gagcttaagc ctcggcgagc     240
tgatctggac atgaaccagc acgtgaataa cgtcacctac attggatggg tgcttgaggt     300
gagtacctta ataaagccta caaaacgtct atcattttaa tcatacatat gagctaacta     360
actattaaat ttgagtttgg ttccctggta atggcagagc atacctcaag aaatcattga     420
tacgcatgag cttcaagtta taactctaga tta                                   453
```

<210> SEQ ID NO 3
<211> LENGTH: 453
<212> TYPE: DNA
<213> ORGANISM: Brassica juncea

<400> SEQUENCE: 3

```
aagttcggga cgagtacttg gttttctgtc ctcgagaacc caggtgaaga agaatcatca      60
tgcttccctt ataattgcta gttaaacagt taatatttaa gcatgtggat ctcaacctgt     120
tgttctctgt atttctcgta gactagcgtt tccagaagag aacaatagca gcttaaagaa     180
aatcccaaaa ctagaagatc cagctcagta ttctatgcta gagcttaagc ctcggcgagc     240
tgatctggac atgaaccagc acgtgaataa cgtcacctac attggatggg tgcttgaggt     300
gagtacctta ataaagccta caaaacgtct atcattttaa tcatacatat gagctaacta     360
actattaaat ttgagtttgg ttccctggta atggcagagc atacctcaag aaatcattga     420
tacgcatgag cttcaagtta taactctaga tta                                   453
```

<210> SEQ ID NO 4
<211> LENGTH: 454
<212> TYPE: DNA
<213> ORGANISM: Brassica napus

<400> SEQUENCE: 4

```
aagttcggga cgagtacttg gttttctgtc ctcgagaacc caggtgaaga agaatcatca     60
tgcttcaata attataattg ctagttaaac agttaatatt taagcatgtg gatctcaatc    120
tgttgttctc tgtatttctc gtagactagc gttttccagaa gagaacaata gcagcttaaa   180
gaaaatccca aaactagaag atccagctca gtattctatg ctagagctta agcctcggcg    240
agctgatctg gacatgaacc agcacgtgaa taacgtcacc tacattggat gggtgcttga    300
ggtgagtata acttaataaa gcctacaaaa cgcctatcat tttaataata catatgagct    360
aactattaaa tttgagtttg gttccctggt aatggcagag catacctcaa gaaatcattg    420
atacgcatga gcttcaagtt ataactctag atta                                454
```

<210> SEQ ID NO 5
<211> LENGTH: 454
<212> TYPE: DNA
<213> ORGANISM: Brassica rapa

<400> SEQUENCE: 5

```
aagttcggga cgagtacttg gttttctgtc ctcgagaacc caggtgaaga agaatcatca     60
tgcttcaata attataattg ctagttaaac agttaatatt taagcatgtg gatctcaacc    120
tgttgttctc tgtatttctc gtagactagc gttttccagaa gagaacaata gcagcttaaa   180
gaaaatccca aaactagaag atccagctca gtattctatg ctagagctta agcctcggcg    240
agctgatctg gacatgaacc agcacgtgaa taacgtcacc tacattggat gggtgcttga    300
ggtgagtata acttaataaa gcctacaaaa cgcctatcat tttaataata catatgagct    360
aactattaaa tttgagtttg gttccctggt aatggcagag catacctcaa gaaatcattg    420
atacgcatga gcttcaagtt ataactctag atta                                454
```

<210> SEQ ID NO 6
<211> LENGTH: 453
<212> TYPE: DNA
<213> ORGANISM: Brassica rapa

<400> SEQUENCE: 6

```
aagttcggga cgagtacttg gttttctgtc ctcgagaacc caggtgaaga agaatcatca     60
tgcttcaata attataattg ctagttaaac agttaatatt taagcatgtg gatctcaacc    120
tgttgttctc tgtatttctc gtagactagc gttttccagaa gagaacaata gcagcttaaa   180
gaaaatccca aaactagagg atccagctca gtattctatg ctagagctta agcctcggcg    240
agctgatctg gacatgaacc agcacgtgaa taacgtcacc tacattggat gggtgcttga    300
ggtgagtata acttaataaa gcctacaaaa cgtctatcat tttaattata catatgagct    360
aactattaaa tttgagtttg gtccctggta atggcagagc atacctcaag aaatcattga    420
tacgcatgag cttcaagtta taactctaga tta                                 453
```

<210> SEQ ID NO 7
<211> LENGTH: 452
<212> TYPE: DNA
<213> ORGANISM: Brassica rapa

<400> SEQUENCE: 7

```
aagttcggga cgagtacttg gttttctgtc ctcgagaacc caggtgaaga agaatcatca     60
tgcttcaata attataattg ctagttaaac agttaatatt taagcatgtg gatctcaacc    120
```

```
tgttgttctc tgtatttctc gtagactagc gtttccagaa gagaacaata gcagcttaaa      180
gaaaatccca aaactagaag atccagctca gtattctatg ctagagctta agcctcggcg      240
agctgatctg gacatgaacc agcacgtgaa taacgtcacc tacattggat gggtgcttga      300
ggtgagtaac ttaataaagc ctacaaaacg tctatcattt taattataca tatgagctaa      360
ctattaaatt tgagtttggt tccctggaaa tggcagagca tacctcaaga aatcattgat      420
acgcatgagc ttcaagttat aactctagat ta                                    452

<210> SEQ ID NO 8
<211> LENGTH: 432
<212> TYPE: DNA
<213> ORGANISM: Brassica juncea

<400> SEQUENCE: 8
aagttcggga cgagtacttg gttttctgtc ctcgagaacc caggtgaaga atcatggttc       60
ccttcaatag ttataatacc ctagttaaac agttatctac catgtaaatc tcaacatgtt      120
gttctctcta tttctcgtag actagcgttt ccggaagaga acaatagcag cttaaagaaa      180
atcccaaaac tagaagatcc agctcagtat tctatgctag gcttaagcc tcggcgagct      240 gatctggaca tgaaccagca gtgaataac gtcacctaca tcggatgggt gcttgaggtg      300
tgtagcccac aaaacgtcta tcattttatt gatgagctaa ctattaaatt tgagtttggt      360
tctctggtaa tggcagagca tacctcaaga aatcattgac acgcatgagc ttcaagttat      420
aactctagat ta                                                          432

<210> SEQ ID NO 9
<211> LENGTH: 432
<212> TYPE: DNA
<213> ORGANISM: Brassica carinata

<400> SEQUENCE: 9
aagttcggga cgagtacttg gttttctgtc ctcgagaacc caggtgaaga atcatggttc       60
ccttcaatag ttataatacc ctagttaaac agttatctac catgtaaatc tcaacatgtt      120
gttctctcta tttctcgtag actagcgttt ccggaagaga acaatagcag cttaaagaaa      180
atcccaaaac tagaagatcc agctcagtat tctatgctag gcttaagcc tcggcgagct      240 gatctggaca tgaaccagca gtgaataac gtcacctaca tcggatgggt gcttgaggtg      300
tgtagcccac aaaacgtcta tcattttatt gatgagctaa ctattaaatt tgagtttggt      360
tctctggtaa tggcagagca tacctcaaga aatcattgac acgcatgagc ttcaagttat      420
aactctagat ta                                                          432

<210> SEQ ID NO 10
<211> LENGTH: 432
<212> TYPE: DNA
<213> ORGANISM: Brassica nigra

<400> SEQUENCE: 10
aagttcggga cgagtacttg gttttctgtc ctcgagaacc caggtgaaga atcatggttc       60
ccttcaatag ttataatacc ctagttaaac agttatctac catgtaaatc tcaacatgtt      120
gttctctcta tttctcgtag actagcgttt ccggaagaga acaatagcag cttaaagaaa      180
atcccaaaac tagaagatcc agctcagtat tctatgctag gcttaagcc tcggcgagct      240 gatctggaca tgaaccagca gtgaataac gtcacctaca tcggatgggt gcttgaggtg      300
tgtagcccac aaaacgtcta tcattttatt gatgagctaa ctattaaatt tgagtttggt      360
```

```
tctctggtaa tggcagagca tacctcaaga aatcattgac acgcatgagc ttcaagttat    420
aactctagat ta                                                       432

<210> SEQ ID NO 11
<211> LENGTH: 445
<212> TYPE: DNA
<213> ORGANISM: Brassica napus

<400> SEQUENCE: 11
aagttcggga cgagtacttg gttttctgtc ctcgagaacc caggtgaaaa agaatcatgc     60
ttcccttcaa taattataat tgctagttaa acagttattt aagcatgtgg atctcaacat    120
gttgttctct gtatttctcg tagactagcg tttccagaag agaacaatag cagcttaaag    180
aaaatcccaa aactagaaga tccagctcag tattctatgc tagagcttaa gcctcggcga    240
gctgatctgg acatgaacca gcacgtgaat aacgtcacct catcggatg ggtgcttgag     300 gtgagtaact taataaagcc ttcaaaacgt ctatcatttt aataatgagc taactattaa    360
atttgagttt ggttccttgg taatggcaga gcatacctca agaaatcatt gatacgcatg    420
agcttcaagt tataactcta gatta                                         445

<210> SEQ ID NO 12
<211> LENGTH: 445
<212> TYPE: DNA
<213> ORGANISM: Brassica oleracea

<400> SEQUENCE: 12
aagttcggga cgagtacttg gttttctgtc ctcgagaacc caggtgaaaa agaatcatgc     60
ttcccttcaa taattataat tgctagttaa acagttattt aagcatgtgg atctcaacat    120
gttgttctct gtatttctcg tagactagcg tttccagaag agaacaatag cagcttaaag    180
aaaatcccaa aactagaaga tccagctcag tattctatgc tagagcttaa gcctcggcga    240
gctgatctgg acatgaacca gcacgtgaat aacgtcacct catcggatg ggtgcttgag     300 gtgagtaact taataaagcc ttcaaaacgt ctatcatttt aataatgagc taactattaa    360
atttgagttt ggttccttgg taatggcaga gcatacctca agaaatcatt gatacgcatg    420
agcttcaagt tataactcta gatta                                         445

<210> SEQ ID NO 13
<211> LENGTH: 445
<212> TYPE: DNA
<213> ORGANISM: Brassica oleracea

<400> SEQUENCE: 13
aagttcggga cgagtacttg gttttctgtc ctcgagaacc caggtgaaaa agaatcatgc     60
ttcccttcaa taattataat tgctagttaa acagatattt aagcatgtgg atctcaacat    120
gttgttctct gtatttctcg tagactagcg tttccagaag agaacaatag cagcttaaag    180
aaaatcccaa aactagaaga tccagctcag tattctatgc tagagcttaa gcctcggcga    240
gctgatctgg acatgaacca gcacgtgaat aacgtcacct catcggatg ggtgcttgag     300 gtgagtaact taataaagcc ttcaaaacgt ctatcatttt aataatgagc taactattaa    360
atttgagttt ggttccttgg taatggcaga gcatacctca agaaatcatt gatacgcatg    420
agcttcaagt tataactcta gatta                                         445

<210> SEQ ID NO 14
```

```
<211> LENGTH: 435
<212> TYPE: DNA
<213> ORGANISM: Brassica oleracea

<400> SEQUENCE: 14
aagttcggga cgagtacttg gttttctgtc ctcgagaacc caggtgaaga agaatcatgc    60
ttcccttcaa taattataat tgctagttaa atagttattt aagcatgtgg atctcaacat   120
gttgttctcg tagactagcg tttccagaag agaacaatag cagcttaaag aaaatcccaa   180
aactagaaga tccagctcag tattctatgc tagagcttaa gcctcggcga gctgatctgg   240
acatgaacca gcacgtgaat aacgtcacgt acatcggatg ggtgcttgag gtgagtaact   300
taataaagcc tacaaaacgt ctattatttt aataatgagg taactattaa atttgagttt   360
ggttctcttg tattggcaga gcatacctca agaaatcatt gatacgcatg agcttcaagt   420
tataactcta gatta                                                    435

<210> SEQ ID NO 15
<211> LENGTH: 435
<212> TYPE: DNA
<213> ORGANISM: Brassica carinata

<400> SEQUENCE: 15
aagttcggga cgagtacttg gttttctgtc ctcgagaacc caggtgaaga agaattatgc    60
ttcccttcaa taattataat tgctagttaa acagttattt aagcatgtgg atctcaacat   120
gttgttctcg tagactagcg tttccagaag agaacaatag cagcttaaag aaaatcccaa   180
aactagaaga tccagctcag tattctatgc tagagcttaa gcctcggcga gctgatctgg   240
acatgaacca gcacgtgaat aacgtcacgt acatcggatg ggtgcttgag gtgagtaact   300
taataaagcc tacaaaacgt ctattatttt aataatgagg taactattaa atttgagttt   360
ggttctcttg taatggcaga gcatacctca agaaatcatt gatacgcatg agcttcaagt   420
tataactcta gatta                                                    435

<210> SEQ ID NO 16
<211> LENGTH: 452
<212> TYPE: DNA
<213> ORGANISM: Brassica juncea

<400> SEQUENCE: 16
aagttcggga cgagtacttg gttttctgtc ctcgagaacc caggtgaaga atcatggttc    60
ccttcaatag ttataatacc ctagttaaac agttatctac catgtaaatc tcaacatgtt   120
gttctctcta tttctcgtag actagcgttt ccggaagaga acaatagcag cttaaagaaa   180
atcccaaaac tagaagatcc agctcagtat tctatgctag agcttaagcc tcggcgagct   240
gatctggaca tgaaccagca cgtgaataac gtcacctaca ttggatgggt gcttgaggtg   300
agtaccttaa taaagcctac aaaacgtcta tcattttaat catacatatg agctaactaa   360
ctattaaatt tgagtttggt tccctggtaa tggcagagca tacctcaaga aatcattgat   420
acgcatgagc ttcaagttat aactctagat ta                                 452

<210> SEQ ID NO 17
<211> LENGTH: 31
<212> TYPE: DNA
<213> ORGANISM: Artificial
<220> FEATURE:
<223> OTHER INFORMATION: primer sequence; 09-O-2812

<400> SEQUENCE: 17
```

```
gacacaaggc ggcttcaaag agttacagat g                                    31

<210> SEQ ID NO 18
<211> LENGTH: 30
<212> TYPE: DNA
<213> ORGANISM: Artificial
<220> FEATURE:
<223> OTHER INFORMATION: primer sequence; 09-0-2813

<400> SEQUENCE: 18
acaatgtcat cttgctggca ttctcttctg                                      30

<210> SEQ ID NO 19
<211> LENGTH: 24
<212> TYPE: DNA
<213> ORGANISM: Artificial
<220> FEATURE:
<223> OTHER INFORMATION: primer sequence; 09-0-3249

<400> SEQUENCE: 19
acagatgaag ttcgggacga gtac                                            24

<210> SEQ ID NO 20
<211> LENGTH: 27
<212> TYPE: DNA
<213> ORGANISM: Artificial
<220> FEATURE:
<223> OTHER INFORMATION: primer sequence; 09-0-3251

<400> SEQUENCE: 20
caggttgaga tccacatgct taaatat                                         27

<210> SEQ ID NO 21
<211> LENGTH: 20
<212> TYPE: DNA
<213> ORGANISM: Artificial Sequence
<220> FEATURE:
<223> OTHER INFORMATION: probe sequence; 09-QP87

<400> SEQUENCE: 21
aagaagaatc atcatgcttc                                                 20

<210> SEQ ID NO 22
<211> LENGTH: 32
<212> TYPE: DNA
<213> ORGANISM: Artificial
<220> FEATURE:
<223> OTHER INFORMATION: primer sequence; 11-0-4046

<400> SEQUENCE: 22
ctcgagaacc caggtgaaga agaatcatca tg                                   32

<210> SEQ ID NO 23
<211> LENGTH: 28
<212> TYPE: DNA
<213> ORGANISM: Artificial
<220> FEATURE:
<223> OTHER INFORMATION: primer sequence; 11-0-4047

<400> SEQUENCE: 23
ccagatcagc tcgccgaggc ttaagctc                                        28

<210> SEQ ID NO 24
<211> LENGTH: 30
<212> TYPE: DNA
```

```
<213> ORGANISM: Artificial
<220> FEATURE:
<223> OTHER INFORMATION: primer sequence; 11-0-4253

<400> SEQUENCE: 24
ttgttctctt ctggaaacgc tagtctacga                                        30

<210> SEQ ID NO 25
<211> LENGTH: 14
<212> TYPE: DNA
<213> ORGANISM: Brassica

<400> SEQUENCE: 25
aatcatcatg cttc                                                         14

<210> SEQ ID NO 26
<211> LENGTH: 15
<212> TYPE: DNA
<213> ORGANISM: Brassica

<400> SEQUENCE: 26
cagttaatat ttaag                                                        15

<210> SEQ ID NO 27
<211> LENGTH: 13
<212> TYPE: DNA
<213> ORGANISM: Brassica

<400> SEQUENCE: 27
ctacattgga tgg                                                          13

<210> SEQ ID NO 28
<211> LENGTH: 15
<212> TYPE: DNA
<213> ORGANISM: Brassica

<400> SEQUENCE: 28
atacatatga gctaa                                                        15

<210> SEQ ID NO 29
<211> LENGTH: 514
<212> TYPE: DNA
<213> ORGANISM: Brassica

<400> SEQUENCE: 29
gacacaaggc ggcttcaaag agttacagat gaagttcggg acgagtactt ggttttctgt       60
cctcgagaac ccaggtgaag aagaatcatc atgcttccct tataattgct agttaaacag      120
ttaatattta agcatgtgga tctcaacctg ttgttctctg tatttctcgt agactagcgt      180
ttccagaaga gaacaatagc agcttaaaga aaatcccaaa actagaagat ccagctcagt      240
attctatgct agagcttaag cctcggcgag ctgatctgga catgaaccag cacgtgaata      300
acgtcaccta cattggatgg gtgcttgagg tgagtacctt aataaagcct acaaaacgtc      360
tatcatttta atcatacata tgagctaact aactattaaa tttgagtttg gttccctggt      420
aatggcagag catacctcaa gaaatcattg atacgcatga gcttcaagtt ataactctag      480
attacagaag agaatgccag caagatgaca ttgt                                  514

<210> SEQ ID NO 30
<211> LENGTH: 515
<212> TYPE: DNA
<213> ORGANISM: Brassica
```

<400> SEQUENCE: 30

```
gacacaaggc ggcttcaaag agttacagat gaagttcggg acgagtactt ggttttctgt      60
cctcgagaac ccaggtgaag aagaatcatc atgcttcaat aattataatt gctagttaaa     120
cagttaatat ttaagcatgt ggatctcaac ctgttgttct ctgtatttct cgtagactag     180
cgtttccaga agagaacaat agcagcttaa agaaaatccc aaaactagaa gatccagctc     240
agtattctat gctagagctt aagcctcggc gagctgatct ggacatgaac cagcacgtga     300
ataacgtcac ctacattgga tgggtgcttg aggtgagtat aacttaataa agcctacaaa     360
acgcctatca ttttaataat acatatgagc taactattaa atttgagttt ggttccctgg     420
taatggcaga gcatacctca agaaatcatt gatacgcatg agcttcaagt tataactcta     480
gattacagaa gagaatgcca gcaagatgac attgt                                 515
```

<210> SEQ ID NO 31
<211> LENGTH: 513
<212> TYPE: DNA
<213> ORGANISM: Brassica

<400> SEQUENCE: 31

```
gacacaaggc ggcttcaaag agttacagat gaagttcggg acgagtactt ggttttctgt      60
cctcgagaac ccaggtgaag aagaatcatc atgcttcaat aattataatt gctagttaaa     120
cagttaatat ttaagcatgt ggatctcaac ctgttgttct ctgtatttct cgtagactag     180
cgtttccaga agagaacaat agcagcttaa agaaaatccc aaaactagaa gatccagctc     240
agtattctat gctagagctt aagcctcggc gagctgatct ggacatgaac cagcacgtga     300
ataacgtcac ctacattgga tgggtgcttg aggtgagtaa cttaataaag cctacaaaac     360
gtctatcatt ttaattatac atatgagcta actattaaat ttgagtttgg ttccctggaa     420
atggcagagc atacctcaag aaatcattga tacgcatgag cttcaagtta taactctaga     480
ttacagaaga gaatgccagc aagatgacat tgt                                   513
```

<210> SEQ ID NO 32
<211> LENGTH: 493
<212> TYPE: DNA
<213> ORGANISM: Brassica

<400> SEQUENCE: 32

```
gacacaaggc ggcttcaaag agttacagat gaagttcggg acgagtactt ggttttctgt      60
cctcgagaac ccaggtgaag aatcatggtt cccttcaata gttataatac cctagttaaa     120
cagttatcta ccatgtaaat ctcaacatgt tgttctctct atttctcgta gactagcgtt     180
tccggaagag aacaatagca gcttaaagaa aatcccaaaa ctagaagatc agctcagta     240
ttctatgcta gggcttaagc ctcggcgagc tgatctggac atgaaccagc atgtgaataa     300
cgtcacctac atcggatggg tgcttgaggt gtgtagccca caaaacgtct atcatttat     360
tgatgagcta actattaaat ttgagtttgg ttctctggta atggcagagc atacctcaag     420
aaatcattga cacgcatgag cttcaagtta taactctaga ttacagaaga gaatgccagc     480
aagatgacat tgt                                                         493
```

<210> SEQ ID NO 33
<211> LENGTH: 506
<212> TYPE: DNA
<213> ORGANISM: Brassica

```
<400> SEQUENCE: 33
gacacaaggc ggcttcaaag agttacagat gaagttcggg acgagtactt ggttttctgt    60
cctcgagaac ccaggtgaaa aagaatcatg cttcccttca ataattataa ttgctagtta   120
aacagttatt taagcatgtg gatctcaaca tgttgttctc tgtatttctc gtagactagc   180
gtttccagaa gagaacaata gcagcttaaa gaaaatccca aaactagaag atccagctca   240
gtattctatg ctagagctta agcctcggcg agctgatctg gacatgaacc agcacgtgaa   300
taacgtcacc tacatcggat gggtgcttga ggtgagtaac ttaataaagc cttcaaaacg   360
tctatcattt taataatgag ctaactatta aatttgagtt tggttccttg gtaatggcag   420 agcataccte aagaaatcat tgatacgcat gagcttcaag ttataactct agattacaga   480
agagaatgcc agcaagatga cattgt                                       506

<210> SEQ ID NO 34
<211> LENGTH: 496
<212> TYPE: DNA
<213> ORGANISM: Brassica

<400> SEQUENCE: 34
gacacaaggc ggcttcaaag agttacagat gaagttcggg acgagtactt ggttttctgt    60
cctcgagaac ccaggtgaag aagaatcatg cttcccttca ataattataa ttgctagtta   120
aatagttatt taagcatgtg gatctcaaca tgttgttctc gtagactagc gtttccagaa   180
gagaacaata gcagcttaaa gaaaatccca aaactagaag atccagctca gtattctatg   240
ctagagctta agcctcggcg agctgatctg gacatgaacc agcacgtgaa taacgtcacg   300
tacatcggat gggtgcttga ggtgagtaac ttaataaagc ctacaaaacg tctattattt   360
taataatgag gtaactatta aatttgagtt tggttctctt gtattggcag agcataccte   420 aagaaatcat tgatacgcat gagcttcaag ttataactct agattacaga agagaatgcc   480
agcaagatga cattgt                                                  496

<210> SEQ ID NO 35
<211> LENGTH: 15
<212> TYPE: DNA
<213> ORGANISM: Brassica

<400> SEQUENCE: 35
ctcaacctgt tgttc                                                    15

<210> SEQ ID NO 36
<211> LENGTH: 26
<212> TYPE: DNA
<213> ORGANISM: Artificial Sequence
<220> FEATURE:
<223> OTHER INFORMATION: CruA 09-O-2809 primer

<400> SEQUENCE: 36
agctcaatgc actggagccg tcacac                                        26

<210> SEQ ID NO 37
<211> LENGTH: 28
<212> TYPE: DNA
<213> ORGANISM: Artificial Sequence
<220> FEATURE:
<223> OTHER INFORMATION: CruA 09-O-2811 primer

<400> SEQUENCE: 37
ggtggctggc taaatcgagg acggaaac                                      28
```

<210> SEQ ID NO 38
<211> LENGTH: 26
<212> TYPE: DNA
<213> ORGANISM: Artificial Sequence
<220> FEATURE:
<223> OTHER INFORMATION: HMG-I/Y 09-0-2807 primer

<400> SEQUENCE: 38
aacgacgcga acggttgcaa caagac                                           26

<210> SEQ ID NO 39
<211> LENGTH: 30
<212> TYPE: DNA
<213> ORGANISM: Artificial Sequence
<220> FEATURE:
<223> OTHER INFORMATION: HMG-I/Y 09-0-2808 primer

<400> SEQUENCE: 39
cgtcaacttt agcaaccaac aggcaccatc                                       30

<210> SEQ ID NO 40
<211> LENGTH: 18
<212> TYPE: DNA
<213> ORGANISM: Artificial Sequence
<220> FEATURE:
<223> OTHER INFORMATION: CruA MDB510

<400> SEQUENCE: 40
ggccagggtt tccgtgat                                                    18

<210> SEQ ID NO 41
<211> LENGTH: 21
<212> TYPE: DNA
<213> ORGANISM: Artificial Sequence
<220> FEATURE:
<223> OTHER INFORMATION: CruA MDB511

<400> SEQUENCE: 41
ccgtcgttgt agaaccattg g                                                21

<210> SEQ ID NO 42
<211> LENGTH: 29
<212> TYPE: DNA
<213> ORGANISM: Artificial Sequence
<220> FEATURE:
<223> OTHER INFORMATION: CruA TM003

<400> SEQUENCE: 42
agtccttatg tgctccactt tctggtgca                                        29

<210> SEQ ID NO 43
<211> LENGTH: 22
<212> TYPE: DNA
<213> ORGANISM: Artificial Sequence
<220> FEATURE:
<223> OTHER INFORMATION: FatA FatA-F

<400> SEQUENCE: 43
ggtctctcag caagtgggtg at                                               22

<210> SEQ ID NO 44
<211> LENGTH: 22
<212> TYPE: DNA
<213> ORGANISM: Artificial Sequence
<220> FEATURE:

<223> OTHER INFORMATION: FatA FatA-R

<400> SEQUENCE: 44
tcgtcccgaa cttcatctgt aa                                    22

<210> SEQ ID NO 45
<211> LENGTH: 25
<212> TYPE: DNA
<213> ORGANISM: Artificial Sequence
<220> FEATURE:
<223> OTHER INFORMATION: FatA FatA-P

<400> SEQUENCE: 45
tgaaccaaga cacaaggcgg cttca                                 25

<210> SEQ ID NO 46
<211> LENGTH: 22
<212> TYPE: DNA
<213> ORGANISM: Artificial Sequence
<220> FEATURE:
<223> OTHER INFORMATION: HMG-I/Y hmg-F

<400> SEQUENCE: 46
ggtcgtcctc ctaaggcgaa ag                                    22

<210> SEQ ID NO 47
<211> LENGTH: 20
<212> TYPE: DNA
<213> ORGANISM: Artificial Sequence
<220> FEATURE:
<223> OTHER INFORMATION: HMG-I/Y hmg-R

<400> SEQUENCE: 47
cttcttcggc ggtcgtccac                                       20

<210> SEQ ID NO 48
<211> LENGTH: 24
<212> TYPE: DNA
<213> ORGANISM: Artificial Sequence
<220> FEATURE:
<223> OTHER INFORMATION: HMG-I/Y hmg-P

<400> SEQUENCE: 48
cggagccact cggtgccgca actt                                  24

<210> SEQ ID NO 49
<211> LENGTH: 22
<212> TYPE: DNA
<213> ORGANISM: Artificial Sequence
<220> FEATURE:
<223> OTHER INFORMATION: BnACCg8 acc1

<400> SEQUENCE: 49
ggtgagctgt ataatcgagc ga                                    22

<210> SEQ ID NO 50
<211> LENGTH: 15
<212> TYPE: DNA
<213> ORGANISM: Artificial Sequence
<220> FEATURE:
<223> OTHER INFORMATION: BnACCg8 acc2

<400> SEQUENCE: 50
ggcgcagcat cggct                                            15

```
<210> SEQ ID NO 51
<211> LENGTH: 32
<212> TYPE: DNA
<213> ORGANISM: Artificial Sequence
<220> FEATURE:
<223> OTHER INFORMATION: BnACCg8 accp

<400> SEQUENCE: 51
aacacctatt agacattcgt tccattggtc ga                                32

<210> SEQ ID NO 52
<211> LENGTH: 21
<212> TYPE: DNA
<213> ORGANISM: Artificial Sequence
<220> FEATURE:
<223> OTHER INFORMATION: PEP pep-F

<400> SEQUENCE: 52
cagttcttgg agccgcttga g                                            21

<210> SEQ ID NO 53
<211> LENGTH: 21
<212> TYPE: DNA
<213> ORGANISM: Artificial Sequence
<220> FEATURE:
<223> OTHER INFORMATION: PEP pep-R

<400> SEQUENCE: 53
tgacggatgt cgagcttcac a                                            21

<210> SEQ ID NO 54
<211> LENGTH: 27
<212> TYPE: DNA
<213> ORGANISM: Artificial Sequence
<220> FEATURE:
<223> OTHER INFORMATION: PEP pep-P

<400> SEQUENCE: 54
acagacctac agccgatgga agcctgc                                      27
```

BRASSICA GENOMIC ASSAYS

FIELD OF THE DISCLOSURE

The present disclosure relates generally to plant molecular biology. More specifically, it relates to the detection of *Brassica* A genomic DNA.

BACKGROUND OF THE DISCLOSURE

*Brassica* species are used as a source of vegetable oil, animal feeds, vegetables and condiments. *Brassica* plants that are used for vegetable production include cabbage, cauliflower, broccoli, kale, kohlrabi, leaf mustard and rutabaga. However, on a world-wide basis, the most economically important use of *Brassica* species is for the production of seed-derived, vegetable oils. The predominant *Brassica* species grown for oil production is *B. napus*, followed by *B. juncea* and *B. rapa*. Seeds of *B. napus*, *B. juncea* and *B. rapa* are referred to as rapeseed. *Brassica* species that are grown primarily for oil production are often called oilseed rape. In North America, canola, a type of oilseed rape that has been selected for low levels of erucic acid and glucosinolates in seeds, is the predominant *Brassica* plant grown for the production of vegetable oil for human consumption.

Canola includes three oilseed *Brassica* species (*B. napus*, *B. rapa*, *B. juncea*) and is grown on over 80 million acres worldwide Canola is a member of the *Brassica* genus which includes a wide variety of plant species that are under commercial cultivation.

Transgenic canola is currently being cultivated worldwide as a means to solve agricultural production problems. With the development of transgenic canola and other transgenic crops, various countries have instituted regulations to identify transgenic material and their derived products. Polymerase chain reaction (PCR) methods have generally been accepted as the method of choice for transgene detection because of its quantitative and qualitative reliability. This method usually requires amplification and detection of a transgene and a corresponding reference gene, and comparing the quantity of the transgene against the quantity of the reference gene. This system requires a set of two primers and a detection probe specific for the transgene and another set of species specific primers and a probe for an endogenous reference gene.

For the purpose of labeling and traceability, transgene detection assays are developed to meet the requirements of various countries. The European Union's Regulation 619/2011 specifies that the results of detection methods be expressed in transgenic mass fraction with respect to a taxon-specific reference system. The target for the "taxon" specific real-time PCR assay needs to not only be taxon specific, but also quantitatively stable in different genetic backgrounds in order to yield stable testing results.

In most crops, the target species for developing a specific PCR assay is unique, such as for *Zea mays*, *Glycine max*, and *Oryza sativa*. For example, in maize (*Zea mays*) fields, there are no other closely-related *Zea* species likely to cross-contaminate a *Zea mays* field and therefore complicate quantification of maize transgenes. However, canola is quite different.

The Triangle of U (FIG. 1) depicts the evolution and relationship between *B. napus*, *B. rapa*, *B. juncea* and three other *Brassica* species (Nagaharu U (1935) Genome analysis in *Brassica* with special reference to the experimental formation of *B. napus* and peculiar mode of fertilization. *Japan. J. Bot* 7: 389-452). Through evolution, the 3 base species (*B. nigra*, *B. oleracea* and *B. rapa*) have combined to form three allotetraploid species (*B. carinata*, *B. napus* and *B. juncea*). The three species where canola exists (*B. juncea*, *B. napus* and *B. rapa*) share the A-genome (FIG. 1).

If an endogenous system can be proven to specifically detect the A-genome, it could provide an endogenous reference system for a variety of applications including the relative quantitation of transgenic canola in *B. juncea*, *B. napus* and *B. rapa*. For example, currently most commercial transgenic canola is *B. napus*, however, an A-specific endogenous reference system could be utilized in detection methods on future transgenics in the other two species (*B. rapa* and *B. juncea*). In addition to being able to detect a wide range of varieties of *B. rapa*, *B. napus* and *B. juncea*, the assay must not detect *B. nigra*, *B. carinata*, *B. oleracea*, and other related species that might contaminate a canola grain lot or other major crops, where such cross-detection reduces the accuracy of the assay. Even more, there are other closely-related *Brassica* relatives that could contaminate canola fields, including, but not limited to, *Camelina sativa*, *Thlaspi arvense*, *Erucastrum gallicum*, *Raphanus raphanistrum*, *Raphanus sativus*, and *Sinapis arvensis*. As such for canola, from a labeling and traceability viewpoint, the challenge is to identify a real-time PCR assay that will be specific to the species that constitute the canola crop.

Several endogenous reference systems currently exist for measuring the relative percentage of genetically modified canola using real-time PCR. However, these systems are not reliable endogenous reference systems (Wu et al., (2010) Comparison of Five Endogenouse Reference Genes for Specific PCR Detection and Quantification of *Brassica napus*, J. Agric. Food Chem, 58: 2812-2817). They are not specific for the taxon or crop of interest, and they have not been shown to be stable across a globally representative sample within the taxon or crop.

This disclosure relates to methods of detection and quantification that are specific to the *Brassica* A-genome and does not significantly cross-react with other *Brassica* species, crops or weedy relatives that could contribute to contamination of a canola field. In addition this endogenous target is stable within each of the three A-genome species when tested on samples from multiple varieties from diverse geographical regions.

SUMMARY

Compositions and methods for detecting, identifying, and quantifying *Brassica* A genomic DNA are provided herein.

A first aspect features a method of detecting and quantifying the amount of *Brassica* A genomic DNA in a sample. The method comprises specifically amplifying a genomic DNA fragment of the *Brassica* A genome, wherein the amplified DNA fragment comprises at least one of the nucleotide sequences of a genomic region selected from the group consisting of SEQ ID NOS: 25, 26, 27, 28, and 35; and, detecting and quantifying the *Brassica* A genome from the amplified fragment of the *Brassica* A genome.

In an embodiment, the amplified fragment of *Brassica* A genome comprises the nucleotide sequence of at least one of SEQ ID NOS: 29, 30, or 31 selected from the group consisting of nucleotide position from about 50 to about nucleotide position 400, 50 to about nucleotide position 100, 50 to about nucleotide position 350, 400 to about nucleotide position 350, 400 to about nucleotide position 200, and 400 to about nucleotide position 100.

In an embodiment, the amplified fragment of *Brassica* A genome comprises (i) the nucleotide sequence of at least one of SEQ ID NOS: 29, 30, or 31; or (ii) a nucleic acid fragment of at least one of SEQ ID NOS: 29, 30, or 31, wherein the nucleic acid fragment is selected from the group consisting of nucleotide position from about 50 to about nucleotide position 400, 50 to about nucleotide position 100, 50 to about nucleotide position 350, 400 to about nucleotide position 350, 400 to about nucleotide position 200, and 400 to about nucleotide position 100 of SEQ ID NOS: 29, 30, or 31.

In an embodiment, the amplification is performed with a primer pair comprising nucleotide sequences selected from the group consisting of SEQ ID NOS: 17, 18, 19, 20, 21, 22, 23, and 24.

In an embodiment, the genomic DNA comprises a FatA gene.

In other embodiments, the amplification does not substantially amplify *Brassica* B and C genomic DNA.

Another aspect features a method of determining the relative amount of a *Brassica* transgenic event in a sample. The method comprises performing a *Brassica* A genome specific polymerase chain reaction, wherein the analysis includes specifically amplifying a genomic DNA fragment of the *Brassica* A genome, wherein the amplified DNA fragment comprises at least one of the nucleotide sequences of a genomic region selected from the group consisting of SEQ ID NOS: 25, 26, 27, 28, and 35; determining the total amount of *Brassica* A genomic DNA in the sample; performing an event specific assay for the transgenic event to determine the amount of the transgenic event in the sample; and, comparing the amount of the transgenic event DNA to the total amount of *Brassica* A genomic DNA in the sample.

In an embodiment, the amplified fragment of *Brassica* A genome comprises the nucleotide sequence of at least one of SEQ ID NOS: 29, 30, or 31 from nucleotide position about 50 to about 400.

In an embodiment, the amplification is performed with a primer pair comprising nucleotide sequences selected from the group consisting of SEQ ID NOS: 17, 18, 19, 20, 21, 22, 23, and 24.

In other embodiments, the genomic DNA comprises a FatA gene.

In an embodiment, the amplification does not substantially amplify *Brassica* B and C genomic DNA.

Another aspect features a method of determining adventitious presence of a *Brassica* transgenic event in a sample. The method comprises obtaining a sample suspected of containing a *Brassica* transgenic event; performing a *Brassica* A genome specific polymerase chain reaction, with a primer, wherein the primer binds to a genomic region of the *Brassica* A genome, the genomic region selected from the nucleotide sequence of at least one of SEQ ID NOS: 29, 30, or 31 from nucleotide position about 50 to about 400; determining the total amount of *Brassica* A genomic DNA in the sample; performing an event specific quantitative assay for the transgenic event to determine the amount of the transgenic event DNA in the sample; and, comparing the amount of the transgenic event to the total amount of *Brassica* in the sample.

In an embodiment, the primer is selected from the group consisting of SEQ ID NOS: 17, 18, 19, 20, 21, 22, 23, and 24.

Another aspect features an amplicon comprising at least one of the nucleotide sequences of a genomic region selected from the group consisting of SEQ ID NOS: 25, 26, 27, 28, and 35 wherein the amplicon is not larger than 500 base pairs.

Another aspect features an oligonucleotide comprising a nucleotide sequence selected from the group consisting of SEQ ID NOS: 17, 18, 19, 20, 21, 22, 23, and 24 wherein the oligo is about 15-500 nucleotides.

Another aspect features a detection kit comprising oligonucleotides comprising a nucleotide sequence selected from the group consisting of SEQ ID NOS: 17, 18, 19, 20, 21, 22, 23, and 24 wherein the oligo is less than about 50 nucleotides and one or more reaction components to perform a quantitative reaction.

Another aspect features a method of determining trait purity of a *Brassica* trait. The method comprises obtaining a sample of a *Brassica* trait; and performing the *Brassica* A genome specific assay by specifically amplifying a genomic DNA fragment of the *Brassica* A genome, wherein the amplified DNA fragment comprises at least one of the nucleotide sequences of a genomic region selected from the group consisting of SEQ ID NOS: 25, 26, 27, 28, and 35; and, detecting and quantifying the *Brassica* A genome from the amplified fragment of the *Brassica* A genome.

In an embodiment, the trait is selected from the group consisting of RT73, RT200, MON88302, DP-073496, HCN92, T45 (HCN28), 23-18-17, 23-198, OXY-235, MS1, MS3, MS6, MS8, RF1, RF2, RF3, and Topas 19/2.

In an embodiment, the determination comprises performing a quantitative polymerase chain reaction.

Another aspect features a method of establishing purity of a *Brassica* seed lot, the method comprising performing a polymerase chain reaction wherein the oligonucleotide primers or probes are capable of discriminating the *Brassica* A genome from the *Brassica* B and C genomes, wherein the oligonucleotide primers and/or probes bind to a target region of the *Brassica* A genome, the target region comprising a nucleotide sequence selected from the group consisting of SEQ ID NOS: 25, 26, 27, 28, and 35.

In an embodiment, the oligonucleotide primers and/or probes comprise a nucleotide sequence selected from the group consisting of SEQ ID NOS: 19, 20, 21, 22, 23, and 24.

Another aspect features a method of quantifying the amount of a transgenic element in a *Brassica* sample. The method comprises performing a polymerase chain reaction wherein the oligonucleotide primers or probes are capable of discriminating the *Brassica* A genome from the *Brassica* B and C genomes, the oligonucleotide primers or probes bind to a target region of the *Brassica* A genome comprising a nucleotide sequence selected from the group consisting of SEQ ID NOS: 29, 30, and 31; performing the transgenic element specific quantitative polymerase chain reaction; and, determining the amount of the transgenic element present in the canola sample by comparing to the amount of *Brassica* A genomic DNA in the sample.

A further aspect features a method of determining seed purity of a seed sample suspected of containing the *Brassica* A genome. The method comprises specifically amplifying a genomic DNA of the *Brassica* A genome, wherein the amplified DNA comprises at least one of the nucleotide sequences of a genomic region selected from the group consisting of SEQ ID NOS: 25, 26, 27, 28, and 35; and, determining the purity of the seed sample based on the presence or absence of the *Brassica* A genome.

In other embodiments, the seed sample contains at least one of broccoli, brussel sprouts, mustard seeds, cauliflower, collards, cabbage, kale, kohlrabi, leaf mustard, or rutabaga.

In other embodiments, the seed sample contains, but is not limited to, broccoli, brussel sprouts, mustard seeds, cauliflower, collards, cabbage, kale, kohlrabi, leaf mustard, or rutabaga.

Another aspect features a method of determining the presence and/or quantity of the *Brassica* A genome. The method comprises specifically hybridizing DNA of the *Brassica* A genome with a probe, wherein the probe selectively binds to at least one of the nucleotide sequences of a genomic region selected from the group consisting of SEQ ID NOS: 25, 26, 27, 28, and 35, optionally under high stringency conditions; and, detecting the presence and/or quantity of the *Brassica* A genome.

In an embodiment, the probe binds the genomic region of the *Brassica* A genome selected from the nucleotide sequence of at least one of SEQ ID NOS: 29, 30, or 31 from nucleotide position about 50 to about 400.

In a further embodiment, the probe comprises the nucleotide sequences of SEQ ID NOS: 19, 20, 21, 22, 23, or 24.

Another aspect features a method of sequencing a region of the *Brassica* A genome. The method comprises obtaining a DNA sample; and, performing a sequencing reaction of the DNA sample wherein the sequenced region comprises at least one of the nucleotide sequences of a genomic region selected from the group consisting of SEQ ID NOS: 25, 26, 27, 28, and 35.

The methods and compositions disclosed herein discriminate detection of *Brassica* A genome as compared to detecting genomic DNA of other genomes (e.g., *Brassica* B and *Brassica* C genomes).

BRIEF DESCRIPTION OF FIGURES AND SEQUENCE LISTING

The disclosure can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIG. 1 shows the triangle of "U" which depicts the relationships between the different plant species of *Brassica* (Nagaharu U (1935) Genome analysis in *Brassica* with special reference to the experimental formation of *B. napus* and peculiar mode of fertilization. *Japan. J. Bot* 7: 389-452). Number of chromosomes is represented by n. *B. nigra, B. oleracea* and *B. rapa* are three base species. Allotetraploid species are *B. carinata, B. juncea*, and *B. napus*.

Figure 2:
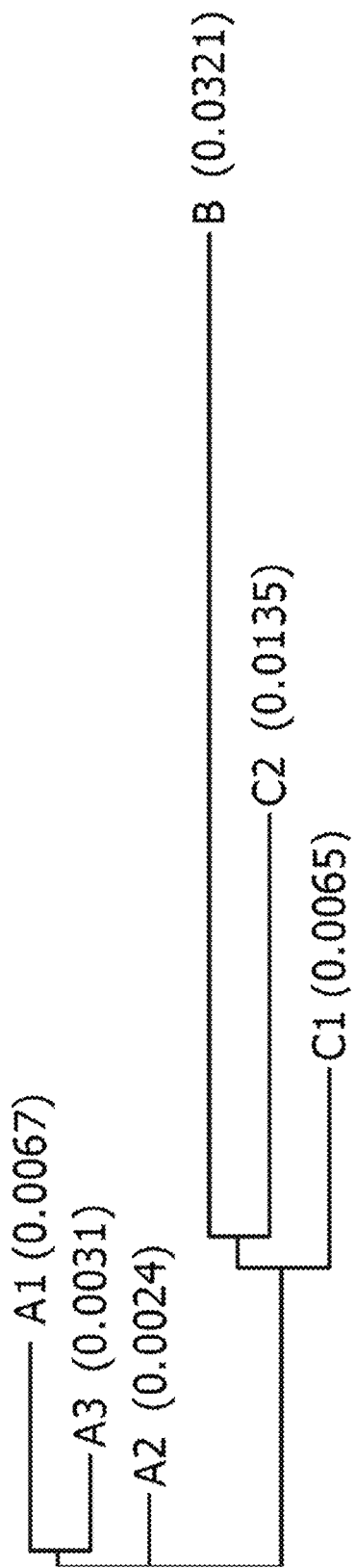

FIG. 2-A shows the evolutionary relationship of the six consensus sequences of FatA.

FIG. 2-B shows the breakdown of the 53 sequenced varieties into the six consensus sequences.

Figure 3:
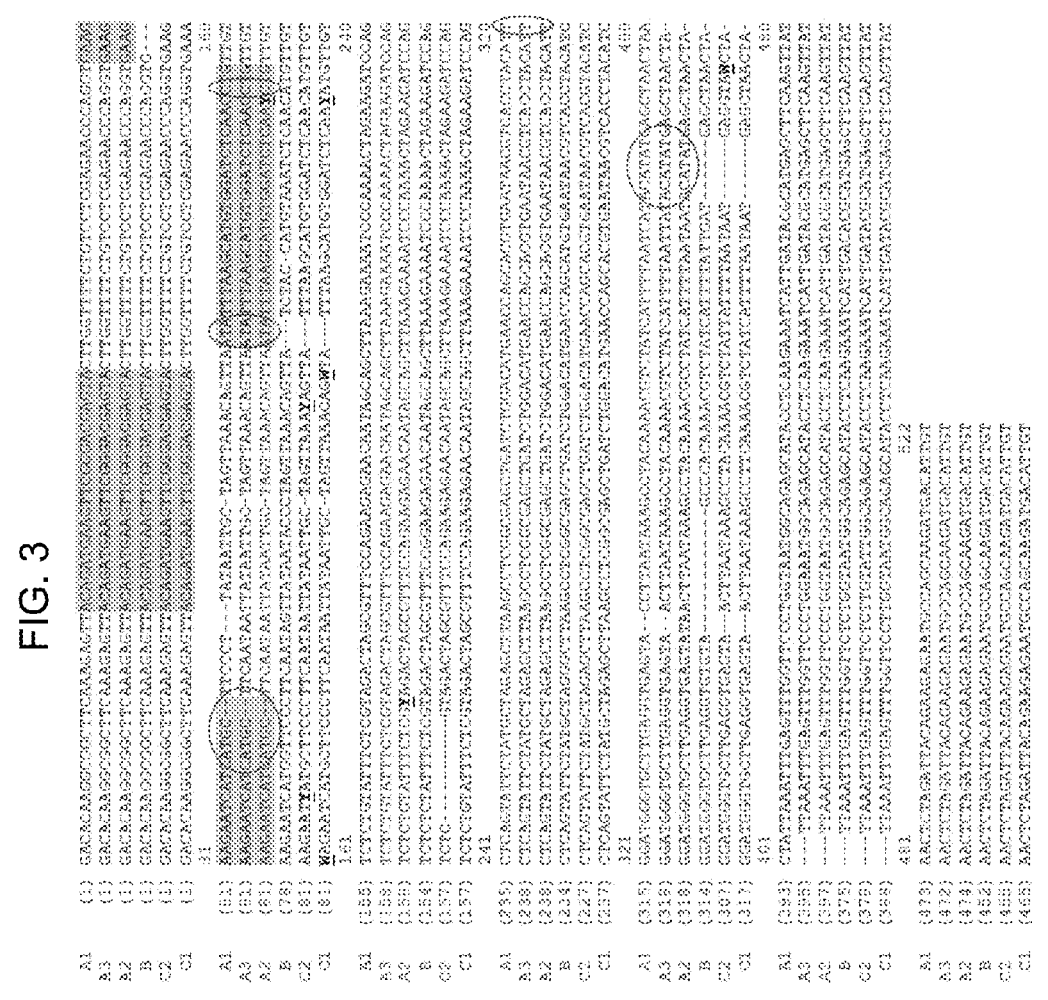

FIG. 3 shows an alignment of the FatA consensus sequences. The circles show regions or bases of A-specificity. The gray highlighted bases show location of the primers and probe for the FatA(A) real-time PCR assay. From left to right: the first, second and third highlighted regions represent the forward primer, the probe, and the reverse primer, respectively. The underline bases show where there are ambiguities within the consensus. The sequences that are aligned in the figure are the A1 sequence (SEQ ID NO: 29), A3 (SEQ ID NO: 31), A2 (SEQ ID NO: 30), B (SEQ ID NO: 32), C2 (SEQ ID NO: 34), and C1 (SEQ ID NO: 33).

The sequence descriptions and Sequence Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. §1.822.

SEQ ID NO:1 is the FatA-A1 consensus nucleotide sequence from *Brassica napus*. Varieties used to create SEQ ID NO: 1 include 45H73, NS1822BC, 46A76, NS5536BC, 43A56, NW1717M, NW4219BC, NW4201BC. 436554, 458967, 531273, 458941, 469735, 458605, 305278, and 633153.

SEQ ID NO: 2 is the FatA-A1.2 consensus nucleotide sequence from *Brassica rapa*. Varieties used to create SEQ ID NO: 2 include Tobin, 257229, 163496, 649190, and 390962.

SEQ ID NO:3 is the FatA-A1.3 consensus nucleotide sequence from *Brassica juncea*. Varieties used to create SEQ ID NO: 3 include JS0917BC, JS0936BC, JS1056BC, JS1260MC, JS1432MC, 418956, 458942, 603011, and 649156.

SEQ ID NO:4 is the FatA-A2.1 consensus nucleotide sequence from *Brassica napus*. Varieties used to create SEQ ID NO:4 include 458954, 469735, and 311729.

SEQ ID NO:5 is the FatA-A2.2 consensus nucleotide sequence from *Brassica rapa*. Varieties used to create SEQ ID NO:5 include 163496, 347600, 346882, and 390962.

SEQ ID NO:6 is the FatA-A2.3 consensus nucleotide sequence from *Brassica rapa*. Varieties used to create SEQ ID NO:6 include Reward.

SEQ ID NO:7 is the FatA-A3.1 consensus nucleotide sequence from *Brassica rapa*. Varieties used to create SEQ ID NO:7 include Tobin, Klondike, Reward, 41P95, 257229, 649159, 163496, and 649190.

SEQ ID NO:8 is the FatA-B.1 consensus nucleotide sequence from *Brassica juncea*. Varieties used to create SEQ ID NO:8 include JS0879BC, JS0917BC, JS0936BC, JS1056BC, JS1260MC, JS1432MC, 418956, 458942, 603011, and 649156.

SEQ ID NO:9 is the FatA-B.2 consensus nucleotide sequence from *Brassica carinata*. Varieties used to create SEQ ID NO:9 include 649155 and 597822.

SEQ ID NO:10 is the FatA-B.3 consensus nucleotide sequence from *Brassica nigra*. Varieties used to create SEQ ID NO:10 include 273638 and 633142.

SEQ ID NO:11 is the FatA-C1.1 consensus nucleotide sequence from *Brassica napus*. Varieties used to create SEQ ID NO:11 include 45H73, NS1822BC, 46A76, NS5536BC, 46A56, NW1717M, NW4219BC, NW4201BC, 436554, 458967, 458954, 531273, 458941, 469735, 458605, 311729, 305278, and 633153.

SEQ ID NO:12 is the FatA-C1.2 consensus nucleotide sequence from *Brassica oleracea*. Varieties used to create SEQ ID NO:12 include 28888, 29800, 365148, 29790, 28852, and 30862.

SEQ ID NO:13 is the FatA-C1.3 consensus nucleotide sequence from *Brassica oleracea*. Varieties used to create SEQ ID NO:13 include 32550.

SEQ ID NO:14 is the FatA-C2.1 consensus nucleotide sequence from *Brassica oleracea*. Varieties used to create SEQ ID NO:14 include 249556, 29041, 29800, 30862, 30724, and 32550.

SEQ ID NO:15 is the FatA-C2.2 consensus nucleotide sequence from *Brassica carinata*. Varieties used to create SEQ ID NO:15 include 649155 and 597822.

SEQ ID NO:16 is the FatA-other consensus nucleotide sequence from *Brassica juncea*. Variety used to create SEQ ID NO:16 include JS1260MC.

SEQ ID NO:17 is the 09-0-2812 primer used to PCR an approximately 500 base product from several varieties from the six *Brassica* species in the Triangle of "U". 09-0-2812 corresponds to position 1500-1530 (5' to 3') for Genbank FatA sequence for *Brassica juncea* Accession No. AJ294419.

SEQ ID NO:18 is the 09-0-2813 primer used to PCR an approximately 500 base product from several varieties from the six *Brassica* species in the Triangle of "U". 09-0-2813 corresponds to position 2226-2197 (5' to 3') for Genbank FatA sequence for *Brassica juncea* Accession No. AJ294419.

SEQ ID NO:19 is the 09-0-3249 assay primer used in the A-specific real time PCR assay SEQ ID NO:20 is the 09-0-3251 FatA A-genome specific real time PCR assay primer.

SEQ ID NO:21 is the 09-QP87 probe for the FatA A-genome specific real time PCR assay.

SEQ ID NO:22 is the 11-0-4046 FatA-A-genome specific gel based PCR assay primer. 11-0-4046 corresponds to position 1782-1813 (5' to 3') for Genbank FatA sequence for *Brassica napus* Accession No. X87842. 11-0-4046 corresponds to position 62-93 (5' to 3') for Genbank FatA sequence for *Brassica juncea* Accession No. AJ294419.

SEQ ID NO:23 is the 11-0-4047 FatA gel-based PCR assay primer. 11-0-4047 corresponds to position 2001-1971 (5' to 3') for the Genbank FatA sequence for *Brassica napus* Accession No. X87842). 11-0-4047 corresponds to position 279-252 (5' to 3') for GenBank FatA sequence for *Brassica juncea* Accession No. AJ294419.

SEQ ID NO:24 is the 11-0-4253 FatA gel-based PCR assay primer. 11-0-4253 corresponds to position 1918-1889 (5' to 3') for the Genbank FatA sequence for *Brassica napua* Accession No. X87842. 11-0-4253 corresponds to position 196-167 (5' to 3') for the Genbank FatA sequence for *Brassica juncea* Accession No. AJ294419.

SEQ ID NO:25 is a 14 nucleotide consensus region of SEQ ID NOS: 29, 30, and 31.

SEQ ID NO:26 is a 15 nucleotide consensus region of SEQ ID NOS: 29, 30, and 31.

SEQ ID NO: 27 is a 13 nucleotide consensus region of SEQ ID NOS: 29, 30, and 31.

SEQ ID NO:28 is a 15 nucleotide consensus region of SEQ ID NOS: 29, 30, and 31.

SEQ ID NO:29 is the A1 consensus sequence used for the alignment.

SEQ ID NO:30 is the A2 consensus sequence used for the alignment.

SEQ ID NO:31 is the A3 consensus sequence used for the alignment.

SEQ ID NO:32 is the B consensus sequence used for the alignment.

SEQ ID NO:33 is the C1 consensus sequence used for the alignment.

SEQ ID NO:34 is the C2 consensus sequence used for the alignment.

SEQ ID NO:35 is a 15 nucleotide consensus region of SEQ ID NOS: 29, 30, and 31.

SEQ ID NO: 36 is the CruA 09-O-2809 primer.
SEQ ID NO: 37 is the CruA 09-O-2811 primer.
SEQ ID NO: 38 is the HMG-I/Y 09-0-2807 primer.
SEQ ID NO: 39 is the HMG-I/Y 09-0-2808 primer.
SEQ ID NO: 40 is the CruA MDB510 forward primer.
SEQ ID NO: 41 is the MDB511 reverse primer.
SEQ ID NO: 42 is the CruA TM003 probe.
SEQ ID NO: 43 is the FatA FatA-F forward primer.
SEQ ID NO: 44 is the FatA FatA-R reverse primer.
SEQ ID NO: 45 is the FatA FatA-P probe.
SEQ ID NO: 46 is the HMG-I/Y hmg-F forward primer.
SEQ ID NO: 47 is the HMG-I/Y hmg-R reverse primer.
SEQ ID NO: 48 is the HMG-I/Y hmg-P probe.
SEQ ID NO: 49 is the BnACCg8 acc1 forward primer.
SEQ ID NO: 50 is the BnACCg8 acc2 reverse primer.
SEQ ID NO: 51 is the BnACCg8 accp probe.
SEQ ID NO: 52 is the PEP pep-F forward primer.
SEQ ID NO: 53 is the PEP pep-R reverse primer.
SEQ ID NO: 54 is the PEP pep-P probe.

DETAILED DESCRIPTION

Methods of detection and quantification that are specific to the *Brassica* A-genome and do not substantially cross-react with other *Brassica* species, crops or weedy relatives that could contribute to contamination of a canola field are disclosed. An endogenous target that is detected is stable within each of the three A-genome species when tested on samples from multiple varieties from diverse geographical regions.

Units, prefixes, and symbols are denoted in their International System of Units (SI) accepted form. Unless otherwise indicated, nucleic acids are written left to right in 5' to 3' orientation; and amino acid sequences are written left to right in amino to carboxy orientation. Numeric ranges recited within the specification are inclusive of the numbers defining the range and include each integer within the defined range. Nucleotides may be referred to herein by their one-letter symbols recommended by the IUPAC-IUBMB Nomenclature Commission. The terms defined below are more fully defined by reference to the specification as a whole. Section headings provided throughout the specification are provided for convenience and are not limitations to the various objects and embodiments of the present disclosure.

The disclosure of each reference set forth herein is hereby incorporated by reference in its entirety, to the extent they relate to the materials and methods described herein.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein, the term "comprising" means "including but not limited to."

"Plant" includes reference to whole plants, plant organs, plant tissues, plant propagules, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

As used herein, the term "canola" refers to a type of *Brassica* having a low level of glucosinolates and erucic acid in the seed. Three canola quality *Brassica* species exist and include *B. napus, B. rapa, B. juncea*.

The terms "dicot" and "dicotyledonous plant" are used interchangeably herein.

The term "dicot" refers to the subclass of angiosperm plants also known as "dicotyledoneae" and includes reference to whole plants, plant organs (e.g., leaves, stems, roots, etc.), seeds, plant cells, and progeny of the same. Plant cell, as used herein includes, without limitation, seeds, suspension cultures, embryos, meristematic regions, callus tissue, leaves, roots, shoots, gametophytes, sporophytes, pollen, and microspores.

The term "transgenic plant" refers to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (i.e., crosses) or by naturally occurring events such as random cross-fertilization, non-recombinant viral infection, non-recombinant bacterial transformation, non-recombinant transposition, or spontaneous mutation.

A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene(s). At the genetic level, an event is part of the genetic makeup of a plant. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

As used herein, "insert DNA" refers to the heterologous DNA within the expression cassettes used to transform the plant material while "flanking DNA" can comprise either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least 20, 50, 100, 200, 300, 400, 1000, 1500, 2000, 2500, or 5000 base pair or greater which is located either immediately upstream of and contiguous with or immediately downstream of and contiguous with the original foreign insert DNA molecule.

As used herein, a "probe" is an isolated polynucleotide to which is attached a conventional detectable label or reporter molecule, e.g., a radioactive isotope, ligand, chemiluminescent agent, enzyme, etc. Such a probe is complementary to a strand of a target polynucleotide, in the instant case, to a strand of isolated DNA from the target sample, from a sample that includes DNA e.g., from the trait of interest. Probes include not only deoxyribonucleic or ribonucleic acids but also polyamides and other probe materials that can specifically detect the presence of the target DNA sequence.

As used herein, "primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primer pairs refer to their use for amplification of a target polynucleotide, e.g., by the polymerase chain reaction (PCR) or other conventional nucleic-acid amplification methods.

"PCR" or "polymerase chain reaction" is a technique used for the amplification of specific DNA segments (see, U.S. Pat. Nos. 4,683,195 and 4,800,159; herein incorporated by reference). Any combination of primers disclosed herein can be used such that the pair allows for the detection of Brassica A-genome.

Probes and primers are of sufficient nucleotide length to bind to the target DNA sequence and specifically detect and/or identify a polynucleotide of interest. It is recognized that the hybridization conditions or reaction conditions can be determined by the operator to achieve this result. This length may be of any length that is of sufficient length to be useful in a detection method of choice. Generally, 8, 11, 14, 16, 18, 20, 22, 24, 26, 28, 30, 40, 50, 75, 100, 200, 300, 400, 500, 600, 700 nucleotides or more, or between about 11-20, 20-30, 30-40, 40-50, 50-100, 100-200, 200-300, 300-400, 400-500, 500-600, 600-700, 700-800, or more nucleotides in length are used. Such probes and primers can hybridize specifically to a target sequence under high stringency hybridization conditions. Probes and primers according to embodiments may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 85%, 90%, 91%, 92%, 93%, 94%, 95%, 96%, 97%, 98%, 99% or greater sequence identity or complementarity to the target polynucleotide, or can differ from the target sequence by 1, 2, 3, 4, 5, 6 or more nucleotides. Probes can be used as primers, but are generally designed to bind to the target DNA or RNA and are not used in an amplification process.

Specific primers can be used to amplify an integration fragment to produce an amplicon that can be used as a "specific probe" or can itself be detected for identifying the polynucleotide of interest in biological samples. Alternatively, a probe can be used during the PCR reaction to allow for the detection of the amplification event (i.e., a Taqman probe or a MGB probe) (so called real time PCR). When the probe is hybridized with the polynucleotides of a biological sample under conditions which allow for the binding of the probe to the sample, this binding can be detected and thus allow for an indication of the presence of an event in the biological sample. Such identification of a bound probe has been described in the art. In an embodiment, the specific probe is a sequence which, under optimized conditions, hybridizes specifically to a region within the 5' or 3' flanking region of the desired location and also may comprise a part of the foreign DNA contiguous therewith. The specific probe may comprise a sequence of at least 80%, between 80 and 85%, between 85 and 90%, between 90 and 95%, and between 95 and 100% identical (or complementary) to a specific region of the target DNA.

As used herein, "amplified DNA" or "amplified fragment" or "amplicon" refers to the product of polynucleotide amplification of a target polynucleotide that is part of a nucleic acid template.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "single nucleotide polymorphism" or "SNP" is a DNA variation occurring when a single nucleotide—A, T, C, or G—in the genome (or other shared sequence) differs between members of a species (or between paired chromosomes in an individual). For example, two sequenced DNA fragments from different individuals, AAGCCTA to AAGCTTA, contain a difference in a single nucleotide. In this case we say that there are two alleles: C and T. Almost all common SNPs have only two alleles.

Alleles may be detected using various techniques (Nakitandwe et al., 2007; herein incorporated by reference).

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

Probes and primers hybridize specifically to a target sequence under stringency hybridization conditions. Hybridization references include, but are not limited to, Herzer and Englert, 2002 Palmisano et al., 2005; herein incorporated by reference.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2× SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system (Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes. As used herein, "amplified DNA" or "amplicon" refers to the product of nucleic acid amplification of a target nucleic acid sequence that is part of a nucleic acid template.

"Genome" as it applies to plant cells encompasses not only chromosomal DNA found within the nucleus, but organelle DNA found within subcellular components (e.g., mitochondrial, plastid) of the cell. Genomic regions refer to a portion of the genome that is targeted to be specifically detected for example, through an amplification reaction or by direct sequencing.

"Heterologous" with respect to sequence means a sequence that originates from a foreign species, or, if from the same species, is substantially modified from its native form in composition and/or genomic locus by deliberate human intervention.

The term "homologous" refers to nucleic acid sequences that are derived from a common ancestral gene through natural or artificial processes (e.g., are members of the same gene family), and thus, typically, share sequence similarity. Typically, homologous nucleic acids have sufficient sequence identity that one of the sequences or its complement is able to selectively hybridize to the other under selective hybridization conditions. The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences have about at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with each other. A nucleic acid that exhibits at least some degree of homology to a reference nucleic acid can be unique or identical to the reference nucleic acid or its complementary sequence.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

Amplification

In vitro amplification techniques are well known in the art. Examples of techniques sufficient to direct persons of skill through such in vitro methods, including the polymerase chain reaction (PCR), the ligase chain reaction (LCR), Qβ-replicase amplification and other RNA polymerase mediated techniques (e.g., NASBA), are found in Berger, Sambrook and Ausubel (all supra) as well as Mullis et al. ((1987) U.S. Pat. No. 4,683,202); *PCR Protocols, A Guide to Methods and Applications* ((Innis et al., eds.) Academic Press Inc., San Diego Academic Press Inc. San Diego, Calif. (1990) (Innis)); Arnheim & Levinson ((Oct. 1, 1990) *C&EN* 36-47); *The Journal Of NIH Research* (1991) 3, 81-94; Kwoh et al. ((1989) *Proc. Natl. Acad. Sci. USA* 86, 1173); Guatelli et al. ((1990) *Proc. Natl. Acad. Sci. USA* 87, 1874); Lomeli et al. ((1989) *J. Clin. Chem.* 35, 1826); Landegren et al. ((1988) *Science* 241, 1077-1080); Van Brunt ((1990) *Biotechnology* 8, 291-294); Wu and Wallace ((1989) *Gene* 4, 560); Barringer et al. ((1990) *Gene* 89, 117), and Sooknanan and Malek ((1995) *Biotechnology* 13: 563-564). Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684, and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

In an embodiment of the disclosure described herein, the amplified fragment of *Brassica* A genome comprises (i) the nucleotide sequence of at least one of SEQ ID NOS: 29, 30, or 31; or (ii) a nucleic acid fragment of at least one of SEQ ID NOS: 29, 30, or 31, wherein the nucleic acid fragment is selected from the group consisting of nucleotide position from about 50 to about nucleotide position 400, 50 to about nucleotide position 100, 50 to about nucleotide position 350, 400 to about nucleotide position 350, 400 to about nucleotide position 200, and 400 to about nucleotide position 100 of SEQ ID NOS: 29, 30, or 31. The amplified fragment of *Brassica* A genome comprises a nucleic acid fragment of at least one of SEQ ID NOS: 29, 30, or 31, wherein the nucleic acid fragment is selected from the group consisting of nucleotide position from about 50 to about nucleotide position 400. This may include, but is not limited to, any single numeric digit interval from about position 50 to about position 400. The nucleic acid fragment may comprise any amplified fragment between and including nucleotide position 50 to nucleotide position 400.

In an embodiment of the disclosure, the detection method comprises sequencing a biological sample containing genomic DNA of *Brassica* A genome, wherein the genomic DNA comprises (i) the nucleotide sequence of at least one of SEQ ID NOS: 29, 30, or 31; or (ii) a nucleic acid fragment of at least one of SEQ ID NOS: 29, 30, or 31, wherein the nucleic acid fragment is selected from the group consisting of nucleotide position from about 50 to about nucleotide position 400, 50 to about nucleotide position 100, 50 to about nucleotide position 350, 400 to about nucleotide position 350, 400 to about nucleotide position 200, and 400 to about nucleotide position 100 of SEQ ID NOS: 29, 30, or 31 or a complement thereof. The portion of the genomic DNA sequenced can be any region within one of SEQ ID NOS: 29, 30, or 31.

The amplicon produced by these methods may be detected by a plurality of methods.

Oligonucleotides for use as primers, e.g., in amplification reactions and for use as nucleic acid sequence probes, are typically synthesized chemically according to the solid phase phosphoramidite triester method described by Beaucage and Caruthers ((1981) *Tetrahedron Lett.* 22:1859), or can simply be ordered commercially.

DNA detection kits can be developed using the compositions disclosed herein and the methods well known in the art.

"Sequence identity" or "identity" in the context of two nucleic acid or polypeptide sequences refers to residues that are the same in both sequences when aligned for maximum correspondence over a specified comparison window.

"Percentage sequence identity" refers to the value determined by comparing two optimally aligned sequences over a comparison window. The percentage is calculated by determining the number of positions at which both sequences have the same nucleotide or amino acid residue, determining the number of matched positions, dividing the number of matched positions by the total number of positions in the comparison window, and multiplying the result by 100 to yield the percentage of sequence identity.

When percentage of sequence identity is used in reference to proteins it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ by conservative substitutions, the percent sequence identity may be adjusted upwards to correct for the conservative nature of the substitution. Sequences that differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller (1988) *Computer Applic. Biol. Sci.* 4:11-17, e.g., as implemented in the program PC/GENE (Intelligenetics, Mountain View, Calif., USA).

Methods of alignment of sequences for comparison are well-known in the art. Optimal alignment of sequences for comparison may be conducted by the local homology algorithm of Smith and Waterman ((1981) *Adv. Appl. Math.* 2:482); by the homology alignment algorithm of Needleman and Wunsch ((1970) *J. Mol. Biol.* 48:443); by the search for similarity method of Pearson and Lipman ((1988) *Proc. Natl. Acad. Sci. USA* 85:2444); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), Madison, Wis., USA; the CLUSTAL program is well described by Higgins and Sharp ((1988) *Gene* 73:237-244); Higgins and Sharp ((1989) *CABIOS* 5:151-153); Corpet et al. ((1988) *Nucleic Acids Research* 16:10881-90); Huang et al. ((1992) *Computer Applications in the Biosciences* 8: 155-65), and Pearson et al. ((1994) *Methods in Molecular Biology* 24:307-331).

The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, e.g., *Current Protocols in Molecular Biology*, Chapter 19, Ausubel et al., Eds., (1995) Greene Publishing and Wiley-Interscience, New York; Altschul et al. (1990) *J. Mol. Biol.* 215:403-410; and, Altschul et al. (1997) *Nucleic Acids Res.* 25:3389-3402.

Software for performing BLAST analyses is publicly available, e.g., through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, e.g., Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-5877). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences that may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen (1993) *Comput. Chem.* 17:149-163) and XNU (Clayerie and States (1993) *Comput. Chem.* 17:191-201) low-complexity filters can be employed alone or in combination.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

EXAMPLES

The following experimental methods and results provide additional details regarding specific aspects of protocols and procedures relevant to the practice of the present disclosure. The examples, which are provided without limitation to illustrate the claimed invention, involve the application of protocols well known to those of skill in the art, and detailed in the references cited herein.

Example 1

Development of A-Genome Specific Endogenous Reference System

Selection of Plant Material

Seeds from various countries were selected from the six Brassica species that make up the Triangle of "U": *B. carinata, B. juncea, B. napus, B. nigra, B. oleracea*, and *B. rapa* (as well as *B. rapa* subspecies) varieties (FIG. 1). Brassica-related species that may be found in or around canola were also included in this study. This includes: *Camelina sitava, Erucastrum gallicum, Thlaspi arvense, Sinapis alba* and *Sinapis arvensis* (as well as *S. arvensis* subspecies). Seeds from other crops were also included: maize, rice, sorghum, tomato, cotton, soybean. The majority of seeds were received from Pioneer Hybrid Inc. in Georgetown, Ontario, Canada and also from USDA (United States Department of Agriculture) in Ames, Iowa and Geneva, N.Y. Table 1 shows the source of seeds used. For those seeds obtained from the USDA, the USDA Accession Numbers (ACNO) are included.

TABLE 1

Seed Sources.

| Species | Source | ACNO (seeds from USDA); Variety name (seeds from Pioneer) |
|---|---|---|
| B. napus | Pioneer | 45H73 |
| | Pioneer | NS1822BC |
| | Pioneer | 46A76 |
| | Pioneer | NS5536BC |
| | Pioneer | 43A56 |
| | Pioneer | NW1717M |
| | Pioneer | NW4219BC |
| | Pioneer | NW4201BC |
| | USDA (Ames, IA) | 436554 |
| | USDA (Ames, IA) | 458967 |
| | USDA (Ames, IA) | 458954 |
| | USDA (Ames, IA) | 531273 |
| | USDA (Ames, IA) | 458941 |
| | USDA (Ames, IA) | 469735 |
| | USDA (Ames, IA) | 458605 |
| | USDA (Ames, IA) | 311729 |
| | USDA (Ames, IA) | 305278 |
| B. rapa | Pioneer | Tobin |
| | Pioneer | Klondike |
| | Pioneer | Reward |
| | Pioneer | 41P95 |
| | USDA (Ames, IA) | 257229 |
| | USDA (Ames, IA) | 633153 |
| | USDA (Ames, IA) | 649159 |
| | USDA (Ames, IA) | 163496 |
| B. rapa ssp dichotoma | USDA (Ames, IA) | 347600 |
| B. rapa ssp oleifera | USDA (Ames, IA) | 649190 |
| B. rapa ssp trilocularis | USDA (Ames, IA) | 346882 |
| B. rapa var. parachinensis | USDA (Ames, IA) | 390962 |
| B. juncea | Pioneer | JS0879BC |
| | Pioneer | JS0917BC |
| | Pioneer | JS0936BC |
| | Pioneer | JS1056BC |

TABLE 1-continued

Seed Sources.

| Species | Source | ACNO (seeds from USDA); Variety name (seeds from Pioneer) |
|---|---|---|
| | Pioneer | JS1260MC |
| | Pioneer | JS1432MC |
| | USDA (Ames, IA) | 418956 |
| | USDA (Ames, IA) | 458942 |
| | USDA (Ames, IA) | 603011 |
| B. oleracea var. alboglabra | USDA (Geneva, NY) | 249556 |
| B. oleracea var. botrytis | USDA (Geneva, NY) | 28888 |
| B. oleracea var. capitata | USDA (Geneva, NY) | 29041 |
| B. oleracea var. costata | USDA (Geneva, NY) | 29800 |
| B. oleracea var. gemmifera | USDA (Geneva, NY) | 365148 |
| B. oleracea var. gongylodes | USDA (Geneva, NY) | 29790 |
| B. oleracea var. italica | USDA (Geneva, NY) | 28852 |
| B. oleracea var. medullosa | USDA (Geneva, NY) | 30862 |
| B. oleracea var. ramosa | USDA (Geneva, NY) | 30724 |
| B. oleracea var. viridis | USDA (Geneva, NY) | 32550 |
| B. nigra | USDA (Ames, IA) | 273638 |
| | USDA (Ames, IA) | 633142 |
| | USDA (Ames, IA) | 649156 |
| | USDA (Ames, IA) | 193960 |
| | USDA (Ames, IA) | 271444 |
| | USDA (Ames, IA) | 633143 |
| | USDA (Ames, IA) | 220282 |
| | USDA (Ames, IA) | 649154 |
| | USDA (Ames, IA) | 280638 |
| | USDA (Ames, IA) | 357369 |
| | USDA (Ames, IA) | 633147 |
| | USDA (Ames, IA) | 131512 |
| | USDA (Ames, IA) | 597829 |
| | USDA (Ames, IA) | 649155 |
| B. carinata | USDA (Ames, IA) | 613124 |
| | USDA (Ames, IA) | 597822 |
| | USDA (Ames, IA) | 360879 |
| | USDA (Ames, IA) | 596534 |
| | USDA (Ames, IA) | 2779 |
| | USDA (Ames, IA) | 193460 |
| | USDA (Ames, IA) | 633076 |
| | USDA (Ames, IA) | 390133 |
| | USDA (Ames, IA) | 209023 |
| | USDA (Ames, IA) | 360882 |
| Sinapis alba | USDA (Ames, IA) | 19266 |
| | USDA (Ames, IA) | 305276 |
| | USDA (Ames, IA) | 311724 |
| | USDA (Ames, IA) | 458960 |
| | USDA (Ames, IA) | 409025 |
| | USDA (Ames, IA) | 633274 |
| Sinapis arvensis | USDA (Ames, IA) | 21449 |
| | USDA (Ames, IA) | 597863 |
| | USDA (Ames, IA) | 633374 |
| Sinapis arvensis subsp. arvensis | USDA (Ames, IA) | 296079 |
| | USDA (Ames, IA) | 407561 |
| | USDA (Ames, IA) | 633411 |
| Erucastrum gallicum | USDA (Ames, IA) | 22990 |
| Raphanus raphanistrum | USDA (Geneva, NY) | 271456 |
| Raphanus sativus | USDA (Geneva, NY) | 268370 |
| Camelina sativa | USDA (Ames, IA) | 650165 |
| Thlaspi arvense | USDA (Ames, IA) | 633414 |
| | USDA (Ames, IA) | 29118 |
| Arabidopsis thaliana Columbia | Pioneer | |

TABLE 1-continued

Seed Sources.

| Species | Source | ACNO (seeds from USDA); Variety name (seeds from Pioneer) |
|---|---|---|
| type | | |
| Gossypium hirsutum | Pioneer | |
| Helianthus annuus | USDA (Ames, IA) | 7451 |
| | USDA (Ames, IA) | 29348 |
| | USDA (Ames, IA) | 592319 |
| Solanum lycopersicum | USDA (Geneva, NY) | 645248 |
| Glycine max | Pioneer | |
| Oryza sativa | Grocery store (USA) | |
| Sorghum bicolor | Pioneer | |
| Zea mays | Pioneer | |

Italicized text denotes seed varieties used for sequencing.
ACNO represents accession number for seeds acquired from USDA.
ACNO = Accession Number;
Note:
Sequences from ACNO 633153 were assigned to both the A and C contigs, suggesting this variety may actually be a *B. napus* (AACC) variety (see Example 3 herein). Two *B. nigra* varieties (ACNO 633142 and ACNO 649156) were assigned to two different consensuses suggesting that these two varieties are not the same species (see Example 3 herein).

Genomic DNA Extraction from Seeds

For consistency, all genomic DNA was extracted from seeds using the same DNA extraction method: a CTAB-based lysis method with passage of the precipitated DNA through a Qiagen Genomic Tip (Qiagen Inc, Valencia, Calif.) for further purification. This DNA extraction protocol was validated in-house for *Zea mays, Gycine max,* and *Brassica napus*. All DNA samples were quantified using a PicoGreen assay (Molecular Probes; Eugene, Oreg.). For the Specificity Comparison of assays, most of the DNAs were tested in a total of 9 reactions (i.e. 3 runs in triplicate). The exceptions are listed in Table 2.

TABLE 2

Exceptions (DNA tested in less than 9 replicates)

| ACNO or Variety name | Species | BnACCg8 | FatA | FatA(A) | HMG-I/Y | PEP |
|---|---|---|---|---|---|---|
| | Arabidopsis thaliana Columbia type | 6 | 4 | 7 | 4 | 4 |
| JS0879BC | Brassica juncea | | 6 | | | |
| JS0917BC | Brassica juncea | | 6 | | | |
| NW4219BC | Brassica napus | | 6 | | | |
| 469735 | | | 6 | | | |
| 193960 | Brassica nigra | 4 | 2 | 2 | 2 | 2 |
| 220282 | | 2 | 2 | 5 | 2 | 2 |
| 357369 | | 2 | 7 | 7 | 7 | 4 |
| 597829 | | | 6 | | | |
| 22990 | Erucastrum gallicum | 6 | 4 | 7 | 4 | 4 |
| 633374 | Sinapis arvensis | 6 | 6 | 6 | 6 | 6 |
| 633414 | Thlaspi arvense | 6 | | | | |

Primers and Probes

The primers used herein were synthesized by Integrated DNA Technologies (Coralville, Iowa), and the probes were synthesized by Applied Biosystems (Carlsbad, Calif.). The sequences of all primers used for generating PCR products for sequencing are listed in Table 3; and the sequences for all primers and probes for the Specificity Testing are listed in Table 4. All probes were labeled as described in the relevant references, except the HMG-I/Y probe 9. Since the SDS2.3 software does not have a detector for HEX, the HMG-I/Y probe was labeled with VIC instead of HEX, since the VIC dye fluoresces in wavelength similar to the HEX dye.

TABLE 3

Primers Used for Generating PCR Products. *B. carinata* or *B. nigra* sequences were not found for CruA, FatA, or HMG-I/Y genes in Genbank.

| | | | Genbank Accession numbers | | | |
|---|---|---|---|---|---|---|
| Gene | Primer/ Probe | Sequence (5' to 3') | *B. napus* (position of forward (f) and reverse ® primers; amplicon size) | *B. rapa* | *B. juncea* | *B. oleracea* |
| CruA | 09-O-2809 | AGCTCAATGCACTGGAGCCGTCACAC (SEQ ID NO: 36) | X1455 (f: 809-834; r: 1555-1528; 747 bp) | KBrHO42K14F | n/a | BOGK186TF |
| | 09-O-2811 | GGTGGCTGGCTAAATCGAGGACGGAAAC (SEQ ID NO: 37) | | | | |
| FatA | 09-O-2812 | GACACAAGGCGGCTTCAAAGAGTTACAGATG (SEQ ID NO: 17) | X87842 (f: 1721-1751; r: 2226-2197; 506 bp) | n/a | BJU278479, AJ294419 | n/a |
| | 09-O-2813 | ACAATGTCATCTTGCTGGCATTCTCTTCTG (SEQ ID NO: 18) | | | | |

TABLE 3-continued

Primers Used for Generating PCR Products. *B. carinata* or *B. nigra* sequences were not found for CruA, FatA, or HMG-I/Y genes in Genbank.

| Gene | Primer/ Probe | Sequence (5' to 3') | B. napus (position of forward (f) and reverse ® primers; amplicon size) | B. rapa | B. juncea | B. oleracea |
|---|---|---|---|---|---|---|
| HMG-I/Y | 09-0-2807 | AACGACGCGAA CGGTTGCAACAA GAC (SEQ ID NO: 38) | AF127919 (f: 176-201; r: 678-649; 503 bp) | KBrB123C07R, KBrB078D23F, KBrB026F21R, CT012477 | n/a | OEG82B0 5.B1, BOMRW 66TR, BONPC3 2TF |
| | 09-0-2808 | CGTCAACTTTAG CAACCAACAGG CACCATC (SEQ ID NO: 39) | | | | |

TABLE 4

Real-time PCR Primers and Probes.

| Gene | Primer/ Probe* | Sequence (5' to 3') | Final conc. (nM) in real-time PCR | Reference |
|---|---|---|---|---|
| CruA | MDB510 | GGCCAGGGTTTCCGTGAT (SEQ ID NO 40) | 200 | 1 |
| | MDB511 | CCGTCGTTGTAGAACCATTGG (SEQ ID NO 41) | 200 | |
| | TM003 | VIC-AGTCCTTATGTGCTCCACTTTCTGGTGC A-TAMRA (SEQ IN NO 42) | 200 | |
| FatA | FatA-F | GGTCTCTCAGCAAGTGGGTGAT (SEQ ID NO 43) | 150 | 2 |
| | FatA-R | TCGTCCCGAACTTCATCTGTAA (SEQ ID NO 44) | 150 | |
| | FatA-P | FAM-ATGAACCAAGACACAAGGCGGCTTCA-TAMRA (SEQ ID NO 45) | 50 | |
| FatA(A)** | 09-0-3249 | ACAGATGAAGTTCGGGACGAGTAC (SEQ ID NO 19) | 300 | Described in this patent application. |
| | 09-0-3251 | CAGGTTGAGATCCACATGCTTAAATAT (SEQ ID NO 20) | 900 | |
| | 09-QP87 | FAM-AAGAAGAATCATCATGCTTC-MGB (SEQ ID NO 21) | 150 | |
| HMG-I/Y | hmg-F | GGTCGTCCTCCTAAGGCGAAAG (SEQ ID NO 46) | 500 | 3 |
| | hmg-R | CTTCTTCGGCGGTCGTCCAC (SEQ ID NO 47) | 500 | |
| | hmg-P** | VIC-CGGAGCCACTCGGTG CCGCAACTT-TAMRA (SEQ ID NO 48) | 300 | |
| BnACCg8 | acc1 | GGTGAGCTGTATAATCGAGCGA (SEQ ID NO 49) | 300 | 4 |
| | acc2 | GGCGCAGCATCGGCT (SEQ ID NO 50) | 300 | |
| | accp | VIC-AACACCTATTAGACATTCGTTCCATTGG TCGA-TAMRA (SEQ ID NO 51) | 200 | |
| PEP | pep-F | CAGTTCTTGGAGCCGCTTGAG (SEQ ID NO 52) | 300 | 5 |
| | pep-R | TGACGGATGTCGAGCTTCACA (SEQ ID NO 53) | 300 | |

TABLE 4-continued

Real-time PCR Primers and Probes.

| Gene | Primer/Probe* | Sequence (5' to 3') | Final conc. (nM) in real-time PCR | Reference |
|------|---------------|---------------------|-----------------------------------|-----------|
|      | pep-P         | FAM-ACAGACCTACAGCCGATGGAAGCCTGC-TAMRA (SEQ ID NO 54) | 200 |           |

Asterisk notes that all probes were labeled as described in the reference, except the HMG-I/Y probe; VIC-TAMRA was used instead of HEX-TAMRA.
Double asterisk notes that FatA(A) describes the A-genome specific assay disclosed herein.

REFERENCES IN TABLE 4

1. EURL method for detection of: 1) T45 (http://gmo-crl.jrc.ec.europa.eu/summaries/T45_validated_RTPCR_method.pdf), 2) MS8 (http://gmo-crl.jrc.ec.europa.eu/summaries/Ms8_validated_Method_Corrected%20version%201.pdf), 3) RF3 (http://gmo-crl.jrc.ec.europa.eu/summaries/Rf3_validated_Method.pdf), and 4) RT73 (http://gmo-crl.jrc.ec.europa.eu/summaries/RT73_validated_Method.pdf)
2. Wu, Y., Wu, G., Xiao, L., Lu, C. Event-Specific Qualitative and Quantitative PCR Detection Methods for Transgenic Rapeseed Hybrids MS1×RF1 and MS1×RF2; J. Agric. Food Chem. 2007, 55, 8380-8389
3. Weng, H.; Yang, L.; Liu, Z.; Ding, J.; Pan, A.; Zhang, D. Novel reference gene, *High-mobility-group protein I/Y*, used in qualitative and real-time quantitative polymerase chain reaction detection of transgenic rapeseed cultivarsl J. AOAC Int. 2005, 88, 577-584
4. Hernandez, M.; Rio, A.; Esteve, T.; Prat, S.; Pla, M. A rapeseed-specific gene, *Acetyl-CoA Carboxylase*, can be used as a reference for qualitative and real-time quantitative PCR detection of transgenes from mixed food samples. J. Agric. Food Chem. 2001, 49, 3622-3627.
5. Zeitler, R.; Rietsch, K.; Vaiblinger, H. Validation of real-time PCR methods for the quantification of transgenic contaminations in rapeseed; Eur Food Res Technol (2002) 214:346-351.

CruA, HMG I/Y and FatA PCR Design and Selection of Template DNAs

In order to design an A-genome specific endogenous real-time PCR assay, three genes were selected: CruA, HMG-I/Y and FatA. Amplification and sequencing of an approximately 500 bp region from these genes from multiple varieties of the six species in the Triangle of "U" was performed. Primers were designed in the identified conserved regions in the available sequences from the six members of the Triangle of "U". Although sequences were not available from all six of the *Brassica* species for all three genes, alignments were made and primers were designed in the conserved regions of the available sequences. Seeds from several varieties (N=38) were selected from various geographical regions in order to capture sequence diversity of the A-genome species (*B. rapa, B. napus,* and *B. juncea*) to develop the assays. The number of varieties sequenced from the remaining 3 species (*B. olearcea, B. carinata,* and *B. nigra*) were less (N=15).

Primer Design for PCR/Cloning/Sequencing Regions of FatA, CruA and HMG Genes

GenBank sequences of FatA, CruA and HMG from the Triangle of "U" species were selected and aligned to find conserved sequences for designing primers and to amplify an approximate 500 bp region from each of these genes. Table 3 shows the Genbank accession number of the sequences used in the alignment, as well as the position and amplicon size of the selected primers (on the *B. napus* accession). No GenBank sequences were available for *B. carinata* and *B. nigra* for these three genes.

Primers were selected to PCR, clone and sequence a region of each gene. For CruA, the selected primers (09-O-2809/09-O-2811) encompass the referenced real-time assay (MDB410, MDB511, TM003), extending 599 bases 5' and 47 bases 3' of the real-time PCR amplicon. For HMG-I/Y the selected primers (09-O-2807/09-O-2808) encompass the referenced real-time assay (hmg-F, hmg-R, hmg-P), extending 273 bases 5' and 131 bases 3' of the real-time PCR amplicon. For FatA, the selected primers (09-O-2812/09-O-2813) are slightly downstream of the FatA assay (FatA-F, FatA-R, FatA-P), omitting 32 bases 5' and extending 462 bases 3' of the real-time PCR amplicon.

PCR, Cleanup and Cloning

Genomic DNA (100-120 ng) isolated from 53 seed varieties (see italicized varieties in Table 1) was used as template for PCRing the region of interest to be cloned and sequenced. The selection of seeds consist of multiple varieties from various geographical regions for *B. napus* (N=17), *B. juncea* (N=9), *B. rapa* (N=12), *B. nigra* (N=3), *B. carinata* (N=2) and *B. oleracea* (N=10). The purified PCR products were cloned into PGEM-T Easy vector. Approximately 6 clones were selected for sequencing using the T7 and SP6 vector primers. In some cases more clones were isolated and sequenced to achieve coverage of both genomes in the allotetraploid species.

Sequence Analysis and Optimization of A-Specific Real-Time PCR Primers and Probe Sequencher v. 4.8 was used for sequence analysis of the cloned PCR products from the CruA, HMG and FatA genes. Alignments of the final contigs were made in Vector NTI. After the design of several primer/probe combinations to be specific to the A-genome of FatA, the optimum primer/probe combination was selected based on A-genome specificity, cycle threshold (Ct) values and PCR efficiency. The optimum primer and probe concentrations were selected based on Ct values, delta Rn values, and PCR efficiency.

Once the assay was optimized, a dilution series was prepared with *B. napus* genomic DNA. A 40 ng/ul dilution of genomic DNA was serially diluted 4 times at 1:2. This dilution series was tested in the optimized real-time assay, using 5 ul of the dilutions (input template DNA in the PCR ranged from 200 ng to 12.5 ng). PCR efficiency and R2 coefficient were evaluated.

Specificity Testing with Six Endogenous Real-Time PCR Assays

Six rapeseed endogenous real-time PCR assays were selected for the specificity testing, including the FatA (A) assay described herein. For consistency, all reactions included 15 ul of a mastermix (including primers, probes, water and 10 ul of Applied Biosystems TaqMan Universal PCR Master Mix w/o AmpErase UNG) and 5 ul of 20 ng/ul genomic DNA (=100 ng genomic DNA) for a final reaction volume of 20 ul. The primer and probe concentrations were as described in the relevant references, and listed in Table 4.

The cycling parameters for the real-time PCR runs were as follows: initial denaturation at 95° C. for 10 minutes; 40 cycles of 95° C. for 15 seconds (denaturation) and 60° C. for 60 seconds (annealing and extension). The real-time PCR runs were performed on 384-well plates in an Applied Biosystems 7900HT instrument. Data was analyzed using Applied Biosystems Sequence Detection Systems (SDS) v. 2.3. For most of the tested samples (see Table 1), the PCR was run in triplicate over three separate real-time PCR runs. Some of the DNA was in limited supply and was run in duplicate and/or less PCR runs. See Table 2 for description of the number of runs and replicates in each of the assays with the DNA that was in limited supply. Varieties NW4219BC, 469735, JS0879BC, JS0917BC, and 597829 had less replicates due to poor PCR results, not lack of DNA.

Example 2

Sequencing Regions of CruA, HMG I/Y and FatA

The primers that were selected resulted in amplification in all six species. To maximize the likelihood that amplification would occur on both genomes within the allotetraploid species (*B. napus, B. juncea* and *B. carinata*), additional clones were selected.

Once the PCR products were cloned from the multiple varieties within the six species, several clones (≥6) were selected for sequencing in order to increase the chance of capturing all potential diversity from the resulting PCR products. For the allotetraploid species, the goal was to obtain sequences from both genomes.

Subsequent to sequence analysis, some additional clones were selected and sequenced in order to fill gaps in genome coverage for the allotetraploid species.

Example 3

Assigning Sequence Data into Consensus Representing Genomes

The consensus sequences were assigned to various consensus groups, and based on overlap of the base species (*B. rapa, B. oleracea* and *B. nigra*) and the allotetraploid species (*B. napus, B. juncea* and *B. carinata*), these were further assigned to either the A, B or C genome. Due to genetic variation of the A, B and C genomes between the species, in some cases more than one consensus sequence was defined for each genome.

CruA

For the CruA sequencing project, two A and two C genome consensus were identified. However, defining a consensus for the B genome was difficult. The cloned PCR products from *B. juncea* (AABB) all fell within the A consensus. In addition, several of the *B. juncea* varieties were difficult to PCR. The two *B. carinata* (BBCC) varieties resulted in cloned PCR products from the C genome only. The difficulty in determining a B consensus may be due to poor binding of the primers to the B genome or the B sequence may not differ significantly from the A consensus. The limited number of varieties from *B. carinata* (BBCC) and *B. nigra* (BB) that were sequenced also may have contributed to difficulty in distinguishing a B consensus. Sequences from ACNO 633153 were assigned to both the A and C contigs, suggesting this variety was mis-typed, and is actually a *B. napus* (AACC) variety.

Two *B. nigra* varieties (ACNO 633142 and ACNO 649156) were assigned to 2 different consensus: 633142 to a non-distinguishing consensus and 649156 to the A consensus, suggesting that these two varieties are not the same species. Within the two A genome consensuses from CruA, there was not a suitable conserved region for the design of a real-time assay.

HMG

For the HMG sequencing project, four A genome consensus, and one C genome consensus were identified. Again, a B consensus could not be identified, either because it could not be distinguished from the A and C consensus, or because it could not be amplified with the PCR primers. All sequences from the *B. juncea* varieties (AABB) were assigned to the A consensus, except ACNO 458942 which was assigned to the A and C. The *B. nigra* varieties (BB) were assigned to the A genome, and the *B. carinata* varieties (BBCC) were assigned to the C consensus. Inability to get a consensus for the B genome could be due to inefficient binding of the primers to the target on the B genome, or overlap with the A consensus. A small sample size of the *B. nigra* and *B. carinata* varieties were sequenced which may have made it more difficult to come up with a B consensus. As for CruA, ACNO 633153 grouped with sequences assigned to the A and C genome consensus. The two *B. nigra* species grouped into two different consensuses: ACNO 633142 did not group in the A or C consensus and ACNO 649156 grouped into the A consensus. A conserved A-genome-specific region could not be identified from the sequenced region of HMG.

FatA

For FatA, there were six consensus sequences: three for the A-genome, two for the C genome, and one for the B genome. The sequence from ACNO 633153 grouped into the C1 and A1 contigs, verifying that it is a *B. napus* and not a *B. rapa* variety. In addition, ACNO 649156 sequence grouped within the A and B consensus, verifying that it is a *B. juncea* variety and not a *B. nigra*. The six consensus sequences from FatA were aligned in VNTI, and the presumed evolutionary relationship of the six sequences is displayed in FIG. 2-A. FIG. 2-B shows the distribution of the various species into the six consensuses.

Example 4

Design and Optimization of A-Specific Real-Time PCR Assay

Several real-time primers and probes were designed in regions conserved among FatA of all three A consensus, and divergent from the FatA of the B and C genomes. The primer/probe set that gave the lowest Ct value and the highest PCR efficiency was selected for further analysis. The selected primers and probe are shown on the consensus alignment in FIG. 3.

After a test for specificity on a smaller set, the real-time PCR assay was optimized. Three runs were performed on a dilution series of DNA from *B. napus* variety 45H73. The results of these runs are shown in Table 5.

TABLE 5

Slope and R2 from 3 real time PCR runs with the FatA(A) assay.

| Run | Slope | R2 | PCR Efficiency (%) |
|---|---|---|---|
| 1 | −3.39 | 0.997 | 97.2 |
| 2 | −3.42 | 0.997 | 96.1 |
| 3 | −3.41 | 0.996 | 96.5 |

Example 5

Specificity Comparison of Six Rapeseed Endogenous Real-Time PCR Assays

To verify that the FatA(A) real-time PCR assay offers greater specificity than existing systems, a panel of DNAs were tested with the Fat(A) assay as well as five other rapeseed endogenous real-time PCR assays. The sources of DNA included: 1) the seed varieties used in the sequence analysis (ACNO 649156 was omitted); 2) additional varieties of *B. carinata* and *B. nigra;* 3) other species that may contaminate canola fields; and 4) seeds from various other crops. The real-time assays were run using the primers and probes (and final concentrations in the reactions) as described in references for the various assays described in Table 4. In most cases the real-time assay was run in triplicate over 3 separate PCR runs. Due to variation in DNA yields, some DNAs were in limited supply and had fewer replicates and/or runs (see Table 2). The average Ct values from this specificity testing is shown in Table 6.

With one exception (*B. nigra* variety ACNO 273638), the FatA(A) assay resulted in average Ct values of ≥35 for all DNAs tested except the *Brassica* species containing the A-genome: *B. napus*, *B. rapa* and *B. juncea* varieties. The average Ct value of the ACNO 273638 *B. nigra* variety in the FatA(A) assay is approximately 9 cycles later than the other A-genome samples, therefore it was possible that this *B. nigra* sample was contaminated with one of the A-genome species. The A genome was not detected during the sequencing of this variety, but if the amplification is due to contaminating A genomic DNA, it is at a very low level based on the delayed Ct value.

All of the other assays tested showed less specificity than the FatA(A) assay; for example, cross reactivity with non-*Brassica* species and/or not specific to the A-genome. BnACCg8 detects the A and B genome and *Sinapis alba*, *Sinapis arvensis* (and *Sinapis arvensis* ssp. *arvensis*); PEP detects the A and C genome; and, and HMG detects primarily the A and B with some cross-reactivity with the C genome and cross reactivity with some of the *Sinapis arvensis* varieties. The CruA assay appears to detect all A, B, and C genomes as well as the related species *Thlaspi arvense*, *Erucastrum gallicum*, *Raphanus raphanistrum*, *Raphanus sativus*, *Sinapis alba*, and *Sinapis arvensis* (and the subspecies: *Sinapis arvensis* ssp. *arvensis*). The FatA assay detects the A, B and C genomes, as well as *Camelina sativa*, *Raphanus raphanistrum*, *Raphanus sativus*, *Sinapis alba*, *Sinapis arvensis* (and the subspecies: *Sinapis arvensis* ssp. *arvensis*) and *Arabidopsis thaliana*.

TABLE 6

Average Ct values with six endogenous real-time PCR systems.

| Species | ACNO or Variety | FatA(A) | BnACCg8 | CruA | FatA | HMG | PEP |
|---|---|---|---|---|---|---|---|
| *B. napus* | 45H73 | 21.2 | 21.9 | 21.9 | 20.3 | 21.5 | 20.1 |
| | NS1822BC | 21.8 | 22.9 | 22.6 | 20.9 | 22.2 | 20.6 |
| | 46A76 | 21.6 | 22.0 | 22.3 | 20.6 | 22.0 | 20.4 |
| | NS5536BC | 22.2 | 22.7 | 23.1 | 21.2 | 22.6 | 21.1 |
| | 43A56 | 22.5 | 23.1 | 23.4 | 21.5 | 23.9 | 21.8 |
| | NW1717M | 21.7 | 22.8 | 22.5 | 20.6 | 27.5 | 21.2 |
| | NW4219BC | 22.1 | 22.6 | 23.0 | 20.5 | 23.6 | 21.5 |
| | NW4201BC | 21.6 | 22.1 | 22.4 | 20.7 | 22.2 | 21.0 |
| | 436554 | 21.9 | 22.6 | 22.9 | 21.0 | 25.5 | 21.3 |
| | 458967 | 21.9 | 22.4 | 22.9 | 20.9 | 26.0 | 21.3 |
| | 458954 | 22.2 | 22.9 | 23.3 | 21.2 | 23.3 | 21.6 |
| | 531273 | 21.9 | 22.9 | 23.3 | 20.8 | 23.4 | 21.5 |
| | 458941 | 21.8 | 23.1 | 22.7 | 20.8 | 23.3 | 21.2 |
| | 469735 | 21.7 | 22.3 | 22.6 | 20.2 | 25.2 | 21.1 |
| | 458605 | 21.8 | 23.0 | 22.7 | 20.9 | 23.4 | 21.0 |
| | 311729 | 22.4 | 22.5 | 23.0 | 21.3 | 22.8 | 21.5 |
| | 305278 | 21.7 | 22.3 | 22.7 | 20.8 | 27.5 | 20.8 |
| *B. rapa* | Tobin | 22.1 | 22.6 | 22.9 | 21.1 | 22.8 | 21.7 |
| | Klondike | 21.0 | 21.3 | 23.0 | 21.8 | 22.4 | 21.1 |
| | Reward | 20.7 | 21.0 | 22.6 | 21.4 | 21.9 | 20.8 |
| | 41P95 | 21.1 | 21.2 | 23.1 | 21.7 | 22.1 | 21.2 |
| | 257229 | 21.6 | 21.7 | 23.6 | 22.5 | 22.7 | 21.8 |
| | 633153 | 21.1 | 22.5 | 23.2 | 22.2 | 23.1 | 21.5 |
| | 649159 | 21.5 | 21.9 | 23.4 | 22.3 | 22.2 | 22.1 |
| | 163496 | 21.2 | 21.7 | 23.4 | 22.0 | 22.4 | 22.1 |
| *B. rapa* ssp *dichotoma* | 347600 | 21.5 | 22.7 | 23.4 | 22.1 | 22.6 | 21.0 |
| *B. rapa* ssp *oleifera* | 649190 | 21.7 | 21.9 | 23.5 | 22.2 | 22.4 | 22.4 |
| *B. rapa* ssp *trilocularis* | 346882 | 21.1 | 23.0 | 23.3 | 21.7 | 22.1 | 20.9 |
| *B. rapa* var. *parachinensis* | 390962 | 21.2 | 23.1 | 23.2 | 22.0 | 21.9 | 22.2 |
| *B. juncea* | JS0879BC | 22.0 | 24.1 | 23.6 | 20.7 | 23.5 | 23.4 |
| | JS0917BC | 22.0 | 23.8 | 23.4 | 20.7 | 23.3 | 23.5 |
| | JS0936BC | 21.9 | 24.0 | 23.9 | 21.4 | 23.7 | 23.4 |
| | JS1056BC | 21.5 | 23.6 | 23.2 | 20.9 | 23.0 | 22.7 |
| | JS1260MC | 21.6 | 23.6 | 23.2 | 20.9 | 23.2 | 22.8 |
| | JS1432MC | 21.7 | 23.5 | 23.2 | 21.0 | 23.2 | 22.9 |
| | 418956 | 21.7 | 23.7 | 23.5 | 20.8 | 23.4 | 23.1 |
| | 458942 | 22.0 | 23.3 | 23.6 | 21.1 | 23.9 | 23.2 |
| | 603011 | 21.7 | 23.8 | 23.5 | 20.9 | 22.9 | 23.2 |

TABLE 6-continued

Average Ct values with six endogenous real-time PCR systems.

| Species | ACNO or Variety | FatA(A) | BnACCg8 | CruA | FatA | HMG | PEP |
|---|---|---|---|---|---|---|---|
| B. oleracea var. alboglabra | 249556 | UDT | UDT | 23.1 | 20.4 | 33.2 | 21.7 |
| B. oleracea var. botrytis | 28888 | UDT | 37.5 | 22.8 | 21.1 | 32.7 | 21.5 |
| B. oleracea var. capitata | 29041 | UDT | 37.5 | 23.3 | 21.1 | 33.2 | 22.2 |
| B. oleracea var. costata | 29800 | UDT | 37.6 | 22.3 | 20.3 | 32.2 | 20.8 |
| B. oleracea var. gemmifera | 365148 | UDT | 37.5 | 22.5 | 20.6 | 31.9 | 21.1 |
| B. oleracea var. gongylodes | 29790 | UDT | 37.1 | 23.2 | 21.3 | 32.7 | 22.1 |
| B. oleracea var. italica | 28852 | UDT | UDT | 27.4 | 25.8 | 35.0 | 26.4 |
| B. oleracea var. medullosa | 30862 | UDT | 38.0 | 22.4 | 20.7 | 31.6 | 21.4 |
| B. oleracea var. ramosa | 30724 | UDT | 37.8 | 22.4 | 20.8 | 31.0 | 21.2 |
| B. oleracea var. viridis | 32550 | UDT | 38.7 | 22.8 | 20.7 | 30.8 | 21.8 |
| B. nigra | 273638 | 30.1 | 25.1 | 24.9 | 19.6 | 25.3 | UDT |
|  | 633142 | 37.0 | 25.4 | 23.6 | 20.0 | 25.1 | UDT |
|  | 193960 | UDT | 30.1 | 26.4 | 23.6 | 31.6 | 21.4 |
|  | 271444 | UDT | 27.7 | 25.0 | 21.0 | 28.0 | UDT |
|  | 633143 | UDT | 25.8 | 23.5 | 20.4 | 27.1 | UDT |
|  | 220282 | UDT | 29.9 | 27.8 | 21.6 | 29.8 | UDT |
|  | 649154 | UDT | 24.8 | 22.4 | 19.5 | 27.3 | UDT |
|  | 280638 | UDT | 26.8 | 26.5 | 20.5 | 27.1 | UDT |
|  | 357369 | 37.4 | 26.7 | 25.3 | 20.5 | 26.9 | UDT |
|  | 633147 | 36.2 | 25.6 | 23.7 | 20.4 | 26.9 | UDT |
|  | 131512 | 37.1 | 26.7 | 25.1 | 20.4 | 27.0 | UDT |
|  | 597829 | UDT | 25.6 | 23.7 | 20.3 | 26.2 | UDT |
|  | 649155 | UDT | 27.3 | 24.2 | 20.5 | 27.8 | UDT |
| B. carinata | 613124 | UDT | 26.7 | 23.1 | 20.7 | 27.8 | 22.3 |
|  | 597822 | UDT | 26.4 | 23.2 | 20.1 | 27.3 | 21.7 |
|  | 360879 | UDT | 25.6 | 25.6 | 19.9 | 26.5 | UDT |
|  | 596534 | UDT | 26.6 | 22.6 | 20.0 | 27.6 | 21.5 |
|  | 2779 | UDT | 27.0 | 23.7 | 20.7 | 27.9 | 22.2 |
|  | 193460 | UDT | 26.7 | 23.4 | 20.8 | 28.5 | 23.0 |
|  | 633076 | UDT | 27.3 | 23.5 | 20.8 | 28.0 | 22.3 |
|  | 390133 | UDT | 26.9 | 22.8 | 20.5 | 27.2 | 22.2 |
|  | 209023 | UDT | 26.9 | 23.4 | 20.4 | 27.7 | 21.9 |
|  | 360882 | UDT | 27.1 | 23.5 | 21.0 | 26.8 | 22.5 |
| Sinapis alba | 19266 | UDT | 27.0 | 24.1 | 21.7 | UDT | UDT |
|  | 305276 | UDT | 29.2 | 23.6 | 22.8 | UDT | UDT |
|  | 311724 | UDT | 27.9 | 23.7 | 21.7 | UDT | UDT |
|  | 458960 | UDT | 27.5 | 23.5 | 22.0 | UDT | UDT |
|  | 409025 | UDT | 29.0 | 24.5 | 21.9 | UDT | UDT |
|  | 633274 | UDT | 25.2 | 23.5 | 20.8 | UDT | UDT |
| Sinapis arvensis | 21449 | UDT | 26.6 | 23.1 | 24.0 | UDT | UDT |
|  | 597863 | UDT | 27.5 | 23.6 | 23.7 | UDT | 30.5 |
|  | 633374 | UDT | 27.1 | 24.4 | 24.6 | 29.5 | UDT |
| Sinapis arvensis subsp. arvensis | 296079 | UDT | 26.5 | 23.6 | 23.9 | 29.5 | UDT |
|  | 407561 | UDT | 26.0 | 22.6 | 23.3 | 29.8 | UDT |
|  | 633411 | UDT | 28.0 | 24.4 | 24.9 | 29.5 | UDT |
| Erucastrum gallicum | 22990 | 37.1 | UDT | 26.1 | 21.0 | UDT | UDT |
| Raphanus raphanistrum | 271456 | UDT | 37.0 | 27.8 | 24.1 | UDT | UDT |
| Raphanus sativus | 268370 | UDT | 35.6 | 27.9 | 24.0 | UDT | UDT |
|  | 650165 | UDT | UDT | UDT | 22.8 | 39.1 | UDT |
| Thlaspi arvense | 633414 | UDT | UDT | 32.1 | UDT | UDT | UDT |
|  | 29118 | UDT | UDT | 31.7 | UDT | UDT | UDT |
| Arabidopsis thaliana Columbia type |  | UDT | UDT | UDT | 29.8 | UDT | 37.7 |
| Gossypium hirsutum |  | UDT | UDT | UDT | 37.3 | UDT | UDT |
| Helianthus | 7451 | 39.0 | UDT | UDT | UDT | UDT | UDT |

TABLE 6-continued

Average Ct values with six endogenous real-time PCR systems.

| Species | ACNO or Variety | FatA(A) | BnACCg8 | CruA | FatA | HMG | PEP |
|---|---|---|---|---|---|---|---|
| annuus | 29348 | UDT | UDT | UDT | UDT | UDT | UDT |
| | 592319 | UDT | UDT | UDT | UDT | UDT | UDT |
| Solanum lycopersicum | 645248 | UDT | UDT | UDT | UDT | UDT | UDT |
| Glycine max | | UDT | UDT | UDT | UDT | UDT | UDT |
| Oryza sativa | | UDT | UDT | UDT | UDT | UDT | UDT |
| Sorghum bicolor | | UDT | UDT | UDT | UDT | UDT | UDT |
| Zea mays | | UDT | UDT | UDT | UDT | UDT | UDT |

UDT represents undetermined, or not detectable in this assay.

Example 6

Testing for Heterogeneity within Each A-Genome Species

In addition to specificity, a desirable endogenous reference system may not exhibit allelic variation among varieties. The FatA(A) assay recognizes the A-genome, and therefore three different species, with varying haploid genome sizes. Therefore, the stability measurements were restricted to the comparison of Ct values of the varieties within each species. By restricting the Ct comparison to those varieties within a species, it eliminates the Ct variation caused by the variation in genome size between the base species (*B. rapa*, AA) and the allotetraplied species (*B. juncea*/AABB and *B. napus*/AACC). The results of this analysis are shown in Table 7. For *B. napus*, the Ct values ranged from 21.6 to 22.5; for *B. rapa* the Ct values ranged from 20.7 to 22.1, and for *B. juncea* the Ct values ranged from 21.5 to 22.0. In the *B. napus* and *B. juncea* species, the Ct range is within 1 Ct value; and for *B. raja* the Ct range is within 1.4 Cts. In all cases the deviation from the mean is within 1 Ct value.

TABLE 7

Heterogeneity Test of FatA (A-genome specific) endogenous reference real-time PCR assay.

| Species | ACNO or Variety name | Mean | Mean (within species) | SD | CV (%) |
|---|---|---|---|---|---|
| *B. napus* | 45H73 | 21.2 | 21.84 | 0.36 | 1.66 |
| | NS1822BC | 21.8 | | | |
| | 46A76 | 21.6 | | | |
| | NS5536BC | 22.2 | | | |
| | 43A56 | 22.5 | | | |
| | NW1717M | 21.7 | | | |
| | NW4219BC | 22.1 | | | |
| | NW4201BC | 21.6 | | | |
| | 436554 | 21.9 | | | |
| | 458967 | 21.9 | | | |
| | 458954 | 22.2 | | | |
| | 531273 | 21.9 | | | |
| | 458941 | 21.8 | | | |
| | 469735 | 21.7 | | | |
| | 458605 | 21.8 | | | |
| | 311729 | 22.4 | | | |
| | 305278 | 21.7 | | | |
| | 633153** | 21.1 | | | |
| *B. rapa* | Tobin | 22.1 | 21.34 | 0.39 | 1.82 |
| | Klondike | 21 | | | |
| | Reward | 20.7 | | | |
| | 41P95 | 21.1 | | | |
| | 257229 | 21.6 | | | |
| | 649159 | 21.5 | | | |
| | 163496 | 21.2 | | | |
| *B. rapa* ssp *dichotoma* | 347600 | 21.5 | | | |
| *B. rapa* ssp *oleifera* | 649190 | 21.7 | | | |
| *B. rapa* ssp *trilocularis* | 346882 | 21.1 | | | |
| *B. rapa* var. *parachinensis* | 390962 | 21.2 | | | |
| *B. juncea* | JS0879BC | 22 | 21.79 | 0.19 | 0.88 |
| | JS0917BC | 22 | | | |
| | JS0936BC | 21.9 | | | |
| | JS1056BC | 21.5 | | | |
| | JS1260MC | 21.6 | | | |
| | JS1432MC | 21.7 | | | |
| | 418956 | 21.7 | | | |
| | 458942 | 22 | | | |
| | 603011 | 21.7 | | | |

Note:
Sequences from ACNO 633153 were assigned to both the A and C contigs, suggesting this variety may actually be a *B. napus* (AACC) variety (see Example 3 herein).

While the foregoing has been described in some detail for purposes of clarity and understanding, it will be clear to one skilled in the art from a reading of this disclosure that various changes in form and detail can be made without departing from the true scope. For example, all the techniques, methods, compositions, apparatus and systems described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of detecting and quantifying the amount of *Brassica* A genomic DNA in a sample, the method comprising:
   (a) amplifying a genomic DNA fragment of the *Brassica* A genome with two or more oligonucleotide primer sequences selected from the group consisting of SEQ ID NOS: 21-24, wherein the amplified DNA fragment comprises at least one of the nucleotide sequences of a genomic region selected from the group consisting of SEQ ID NOS: 25, 26, 27, and 28, and wherein SEQ ID NOS: 25, 26, 27, and 28 of the amplified fragment identifies the presence of *Brassica* A genome in the sample; and
   (b) detecting the amplified DNA fragment and quantifying the *Brassica* A genome from the amplified DNA fragment of the *Brassica* A genome.

2. The method of claim 1, wherein the amplified fragment of *Brassica* A genome comprises (i) the nucleotide sequence of at least one of SEQ ID NOS: 29, 30, or 31; or (ii) a nucleic acid fragment of at least one of SEQ ID NOS: 29, 30, or 31, wherein the nucleic acid fragment is selected from the group consisting of nucleotide position from about 50 to about nucleotide position 400, 50 to about nucleotide position 100, 50 to about nucleotide position 350, 400 to about nucleotide position 350, 400 to about nucleotide position 200, and 400 to about nucleotide position 100 of SEQ ID NOS: 29, 30, or 31.

3. The method of claim 1, wherein the genomic DNA comprises a FatA gene.

4. The method of claim 1 wherein the amplified fragment of *Brassica* A genome comprises the nucleotide sequence of at least one of SEQ ID NOS. 29, 30, or 31 from nucleotide position about 50 to about 400.

5. A method of determining the relative amount of a *Brassica* transgenic event in a sample, the method comprising:
   (a) performing a *Brassica* A genome specific polymerase chain reaction with two or more oligonucleotide primer sequences selected from the group consisting of SEQ ID NOS: 21-24, wherein the reaction includes specifically amplifying a genomic DNA fragment of the *Brassica* A genome, wherein the amplified DNA fragment comprises at least one of the nucleotide sequences of a genomic region selected from the group consisting of SEQ ID NOS: 25, 26, 27, and 28;
   (b) determining the total amount of *Brassica* A genomic DNA in the sample;
   (c) performing an event specific assay for the transgenic event to determine the amount of the transgenic event in the sample; and
   (d) comparing the amount of the transgenic event DNA to the total amount of *Brassica* A genomic DNA in the sample.

6. The method of claim 5, wherein the genomic DNA comprises a FatA gene.

7. The method of claim 5, wherein the determination comprises performing a quantitative polymerase chain reaction.

8. A method of determining an adventitious presence of a *Brassica* transgenic event in a sample, the method comprising:
  (a) obtaining a sample suspected of containing a *Brassica* transgenic event;
  (b) performing a *Brassica* A genome specific polymerase chain reaction, with two or more primers selected from the group consisting of SEQ ID NOS: 21-24, wherein the primers bind to a genomic region of the *Brassica* A genome, the genomic region selected from the nucleotide sequence of at least one of SEQ ID NOS: 29, 30; or 31 from nucleotide position about 50 to about 400 and wherein the genomic region comprising one of SEQ ID NOS: 25-28 is amplified;
  (c) determining the total amount of *Brassica* A genomic DNA in the sample;
  (d) performing an event specific quantitative assay for the transgenic event to determine the amount of the transgenic event DNA in the sample; and
  (e) comparing the amount of the transgenic event to the total amount of *Brassica* in the sample.

9. A method of establishing purity of a *Brassica* seed lot, the method comprising performing a polymerase chain reaction wherein the polymerase chain reaction comprises two or more oligonucleotide primers or probes capable of discriminating the *Brassica* A genome from the *Brassica* B and C genomes, wherein the oligonucleotide primers and/or probes is selected from the group comprising SEQ ID NOS: 21-24 and bind to a target region of the *Brassica* A genome, the target region comprising a nucleotide sequence selected from the group consisting of SEQ ID NOS: 25, 26, 27, and 28, and thereby quantifying *Brassica* A genome DNA in said *Brassica* seed lot.

10. The method of claim 9, wherein the oligonucleotide primers and/or probes comprise a nucleotide sequence selected from the group consisting of SEQ ID NOS: 21, 22, 23, and 24.

11. A method of quantifying the amount of a transgenic element in a *Brassica* sample, the method comprising:
  (a) performing a polymerase chain reaction wherein the polymerase chain reaction comprises two or more oligonucleotide primers or probes selected from the croup consisting of SEQ ID NOS: 21-24 that are capable of discriminating the *Brassica* A genome from the *Brassica* B and C genomes, the oligonucleotide primers or probes bind to a target region of the *Brassica* A genome comprising a nucleotide sequence selected from the group consisting of SEQ ID NOS: 29, 30, and 31, and wherein the target *Brassica* A genome comprising one of SEQ ID NOS: 25-28 is amplified and thereby quantifying *Brassica* A genome DNA in the sample;
  (b) performing a second polymerase chain reaction to detect the transgenic element present in the sample; and
  (c) determining the relative amount of the transgenic element present in the *Brassica* sample by comparing amount of the transgenic element present in the sample to the amount of *Brassica* A genomic DNA in the sample.

12. A method of determining seed purity of a seed sample suspected of containing the *Brassica* A genome, the method comprising:
  (a) specifically amplifying a genomic DNA of the *Brassica* A genome with two or more oligonucleotide primers selected from the group consisting of SEQ ID NOS: 21-24, wherein the amplified DNA comprises at least one of the nucleotide sequences of a genomic region selected from the group consisting of SEQ ID NOS: 25, 26, 27, and 28; and
  (b) determining the purity of the seed sample based on the presence or absence of the *Brassica* A genome.

13. The method of claim 12, wherein the seed sample contains at least one of broccoli, brussel sprouts, mustard seeds, cauliflower, collards, cabbage, kale, kohlrabi, leaf mustard, or rutabaga.

14. A method of determining the presence and/or quantity of the *Brassica* A genome, the method comprising:
  (a) specifically hybridizing DNA of the *Brassica* A genome with a probe, wherein the probe selectively binds to at least one of the nucleotide sequences of a genomic region selected from the group consisting of SEQ ID NOS: 25, 26, 27, and 28, optionally under high stringency conditions, and;
  (b) detecting the presence and/or quantity of the *Brassica* A genome.

15. The method of claim 14, wherein the probe binds the genomic region of the *Brassica* A genome selected from the nucleotide sequence of at least one of SEQ ID NOS: 29, 30, or 31 from nucleotide position about 50 to about 400.

16. The method of claim 14, wherein the probe comprises the nucleotide sequences of SEQ ID NOS: 21, 22, 23, or 24.

* * * * *